United States Patent
Kaneko et al.

(10) Patent No.: US 11,037,294 B2
(45) Date of Patent: Jun. 15, 2021

(54) IMAGE PROCESSING DEVICE, IMAGE PROCESSING METHOD, AND COMPUTER-READABLE RECORDING MEDIUM

(71) Applicant: OLYMPUS CORPORATION, Tokyo (JP)

(72) Inventors: Yoshioki Kaneko, Hachioji (JP); Takeshi Otsuka, Tokyo (JP); Zhen Li, Hino (JP)

(73) Assignee: OLYMPUS CORPORATION, Tokyo (JP)

(*) Notice: Subject to any disclaimer, the term of this patent is extended or adjusted under 35 U.S.C. 154(b) by 44 days.

(21) Appl. No.: 16/460,174

(22) Filed: Jul. 2, 2019

(65) Prior Publication Data

US 2019/0325577 A1    Oct. 24, 2019

Related U.S. Application Data

(63) Continuation of application No. PCT/JP2017/000624, filed on Jan. 11, 2017.

(51) Int. Cl.
*G06K 9/00* (2006.01)
*G06T 7/00* (2017.01)
(Continued)

(52) U.S. Cl.
CPC ....... *G06T 7/0012* (2013.01); *G01N 15/1463* (2013.01); *G06T 7/162* (2017.01);
(Continued)

(58) Field of Classification Search
CPC .................................................. G06T 7/0012
See application file for complete search history.

(56) References Cited

U.S. PATENT DOCUMENTS

2011/0057946 A1* 3/2011 Yamamoto ........... G06K 9/4652
345/589
2012/0033064 A1    2/2012 Yamada et al.
(Continued)

FOREIGN PATENT DOCUMENTS

JP    2012-037432 A    2/2012
JP    2012-122852 A    6/2012
(Continued)

OTHER PUBLICATIONS

International Search Report dated Apr. 4, 2017 issued in PCT/JP2017/00624.
Abstract of JP 2011-179924 A, dated Sep. 15, 2011.

*Primary Examiner* — Oneal R Mistry
(74) *Attorney, Agent, or Firm* — Scully, Scott, Murphy & Presser, P.C.

(57) ABSTRACT

An image processing device includes a processor including hardware. The processor is configured to: sequentially perform, on all at least two types of stains, an extraction process to extract a stained area due to a target stain from a single stain image of the target stain, starting from a stain having high specificity with regard to a target site; and sequentially perform a correction process, on all at least one type of second stain except for a first stain having the highest specificity among the at least two types of stains, to correct the single stain image by excluding stained areas of all stains having higher specificity than the target stain from the single stain image of the target stain, starting from the stain having the high specificity.

20 Claims, 18 Drawing Sheets

(51) Int. Cl.
*G06T 7/162* (2017.01)
*G01N 15/14* (2006.01)
*G06T 5/10* (2006.01)
(52) U.S. Cl.
CPC ........ *G01N 2015/1486* (2013.01); *G06T 5/10* (2013.01); *G06T 2207/30024* (2013.01)

(56) References Cited

U.S. PATENT DOCUMENTS

| | | | | |
|---|---|---|---|---|
| 2012/0327211 | A1* | 12/2012 | Yamamoto | G16H 10/40 |
| | | | | 348/79 |
| 2013/0182936 | A1 | 7/2013 | Yoshihara et al. | |
| 2014/0270457 | A1* | 9/2014 | Bhargava | G06T 7/0014 |
| | | | | 382/133 |
| 2017/0323148 | A1* | 11/2017 | Sarkar | G06K 9/00127 |
| 2018/0101949 | A1* | 4/2018 | Wang | G01N 15/0205 |

FOREIGN PATENT DOCUMENTS

| | | |
|---|---|---|
| JP | 5490568 B2 | 5/2014 |
| WO | 2012/043498 A1 | 4/2012 |
| WO | 2016/104308 A1 | 6/2016 |

* cited by examiner

IMAGE PROCESSING DEVICE, IMAGE PROCESSING METHOD, AND COMPUTER-READABLE RECORDING MEDIUM

CROSS-REFERENCE TO RELATED APPLICATION

This application is a continuation of International Application No. PCT/JP2017/000624, filed on Jan. 11, 2017, the entire contents of which are incorporated herein by reference.

BACKGROUND

1. Technical Field

The present disclosure relates to an image processing device, an image processing method, and a computer-readable recording medium to process a stained-specimen image that captures a stained specimen.

2. Related Art

Spectral transmittance is one of the physical quantities representing the physical property unique to an object. Spectral transmittance is the physical quantity that represents the ratio of transmitted light to incident light at each wavelength, and it is information unique to an object and its values are not changed due to extrinsic influences unlike color information such as RGB values that depend on changes in illumination light. For this reason, the spectral transmittance is used in various fields as information for reproducing the color of the object itself. For example, in the fields of pathological diagnosis using a living tissue specimen, particularly a pathological specimen, the spectral transmittance is used as an example of the spectral characteristic value for analysis of an image that captures the specimen.

As one of the pathological diagnosis, tissue diagnosis is known, which is to collect tissue in a lesion area and observe it with a microscope so as to diagnose a disease or examine how much the lesion is expanding. This tissue diagnosis is also called biopsy, and it is popular that a block specimen obtained after extraction of an organ or a pathological specimen obtained after biopsy using a needle is sliced in a thickness of approximately several micrometers and then it is enlarged and observed by using a microscope so as to obtain various findings. Especially, transmission observation using an optical microscope is one of the most popular observation methods because of relatively inexpensive equipment, easy handling, and conventionality in practice. In this case, a sliced specimen hardly causes light absorption and scattering and it is almost colorless and transparent; therefore, it is typical to conduct staining using a dye prior to observation.

Various staining techniques are proposed, and there are more than 100 types in total; particularly for pathological specimens, hematoxylin-eosin staining (hereafter, referred to as "HE staining") using two dyes, hematoxylin in blue-violet and eosin in red, is typically used.

Hematoxylin is a natural substance collected from plants, and it does not have staining properties. However, its oxidized material, hematin, is a basophilic dye, and it binds with a negatively charged substance. As deoxyribonucleic acid (DNA) included in a cell nucleus is negatively charged due to the phosphate group included as a component, it binds with hematin so as to be stained in blue-violet. As described above, it is not hematoxylin but hematin, its oxidized material, that has staining properties; however, as it is typical to use hematoxylin as the name of the stain, it is hereafter used.

Meanwhile, eosin is an acidophilic dye, and it binds with a positively charged substance. The pH environment has an effect on whether an amino acid or a protein is charged positively or negatively, and under the acidic environment, it is more likely to be positively charged. For this reason, acetic acid is sometimes added to an eosin solution for use. A protein included in a cytoplasm binds with eosin so as to be stained in red to pink.

In a specimen (hereafter, referred to as stained specimen) after HE staining, cell nuclei, bone tissue, and the like, are stained in blue-violet, cytoplasm, connective tissue, red blood cells, and the like, are stained in red so that they may be easily visually recognized. As a result, an observer is capable of determining the size, the positional relationship, and the like, of elements included in tissue, such as cell nuclei, and is capable of morphologically judging the state of a stained specimen.

Observation of a stained specimen is conducted by not only observer's eyes but also multiband capturing of the stained specimen and presentation on the display screen of an external device. In the case of display on the display screen, for example, a process is performed to estimate the spectral transmittance at each point on a stained specimen based on a captured multiband image, or a process is performed to estimate the quantity of dye with which the stained specimen is stained based on the estimated spectral transmittance, and a display image which is an RGB image of the stained specimen for display is composed.

Techniques for estimating the spectral transmittance at each point on the stained specimen based on a multiband image of the stained specimen include, for example, an estimation technique using analysis of principal component and an estimation technique using Wiener estimation. Wiener estimation is widely known as one of the linear filtering techniques to estimate original signals from observed signals having noise superimposed thereon, and it is a technique to minimize errors in consideration of statistical properties of the observation target and properties of noise (observed noise). As signals from a camera contain some noise, Wiener estimation is extremely useful as a technique to estimate original signals.

An explanation is given below of a conventional method of composing a display image from a multiband image of a stained specimen.

First, a multiband image of the stained specimen is captured. For example, 16 bandpass filters are rotated by a filter wheel and switched so that a multiband image is captured in sequential lighting. Thus, a multiband image having pixel values in 16 bands at each point on the stained specimen is obtained. Although a dye is supposed to be distributed in three dimensions within the stained specimen, which is the target to be observed, it is difficult to directly capture it as a three-dimensional image with the normal transmission observation system, and it is observed as a two-dimensional image that is obtained by projecting the illumination light, passed through the stained specimen, onto the imaging element of the camera. Therefore, each point mentioned here refers to a point on the stained specimen, corresponding to each pixel of the imaging element projected.

Here, with regard to any point (pixel) x of a captured multiband image, the relation between the pixel value $g(x,b)$ in the band b and the spectral transmittance $t(x,\lambda)$ at the corresponding point on the stained specimen satisfies the following Equation (1) based on the response system of the camera.

$$g(x,b)=\int_\lambda f(b,\lambda)s(\lambda)e(\lambda)t(x,\lambda)d\lambda+n(b) \quad (1)$$

In Equation (1), $\lambda$ denotes the wavelength, $f(b,\lambda)$ denotes the spectral transmittance of the b-th bandpass filter, $s(\lambda)$ denotes the spectral sensitivity property of the camera, $e(\lambda)$ denotes the spectral radiant property of illumination, and $n(b)$ denotes observed noise in the band b. As b is a serial number for identifying a band, and it is here an integer number that satisfies $1 \leq b \leq 16$. The actual calculation uses the following Equation (2) in which Equation (1) is discretized in a wavelength direction.

$$G(x)=FSET(x)+N \quad (2)$$

In Equation (2), when the number of sample points in the wavelength direction is D and the number of bands is B (here, B=16), $G(x)$ is the matrix in the row B and the column 1 corresponding to the pixel value $g(x,b)$ at the point x. Similarly, $T(x)$ is the matrix in the row D and the column 1 corresponding to $t(x,\lambda)$, and F is the matrix in the row B and the column D corresponding to $f(b,\lambda)$. Furthermore, S is the diagonal matrix in the row D and the column D, and the diagonal element corresponds to $s(\lambda)$. Similarly, E is the diagonal matrix in the row D and the column D, and the diagonal element corresponds to $e(\lambda)$. N is the matrix in the row B and the column 1 corresponding to $n(b)$. In Equation (2), as equations regarding multiple bands are summarized by using a matrix, the variable b representing a band is not described. Moreover, the integrate regarding the wavelength $\lambda$ is replaced with the product of matrices.

Here, to simplify description, the matrix H defined by the following Equation (3) is introduced. The matrix H is also called a system matrix.

$$H=FSE \quad (3)$$

Therefore, Equation (2) is replaced with the following Equation (4).

$$G(x)=HT(x)+N \quad (4)$$

Then, by using Wiener estimation, the spectral transmittance at each point on the stained specimen is estimated based on a captured multiband image. The estimated value of the spectral transmittance (hereafter, referred to as spectral transmittance data) $\hat{T}(x)$ is calculatable by using the following Equation (5). Here, $\hat{T}$ indicates that the symbol "^ (hat)" indicating an estimated value is attached to the upper section of T.

$$\hat{T}(x)=WG(x) \quad (5)$$

In Equation (5), W is represented by using the following Equation (6), and it is called "Wiener estimation matrix" or "estimation operator used for Wiener estimation".

$$W=R_{SS}H^T(HR_{SS}H^T+R_{NN})^{-1} \quad (6)$$

In Equation (6), $R_{SS}$ is the matrix in the row D and the column D, and it represents the autocorrelation matrix of the spectral transmittance of the stained specimen. Furthermore, $R_{NN}$ is the matrix in the row B and the column B, and it represents the autocorrelation matrix of noise of the camera used for capturing. Furthermore, with regard to any matrix X, the matrix $X^T$ represents the transposed matrix of the matrix X, and the matrix $X^{-1}$ represents the inverse matrix of the matrix X. The matrices F, S, E, i.e., the spectral transmittance of the bandpass filter, the spectral sensitivity property of the camera, and the spectral radiant property of the illumination, constituting the system matrix H, the matrix $R_{SS}$, and the matrix $R_{NN}$ are previously acquired.

As described above, after the spectral transmittance data $\hat{T}(x)$ is estimated, the quantity of dye at the corresponding point (hereafter, referred to as sample point) on the stained specimen is estimated based on the spectral transmittance data $\hat{T}(x)$. Here, the target dyes to be estimated are three types, i.e., hematoxylin, eosin with which a cytoplasm is stained, eosin with which a red blood cell is stained, or the inherent pigment of a red blood cell that is not stained, and they are abbreviated as H dye, E dye, and R dye, respectively. Strictly speaking, red blood cells have the inherent color although it is not stained, and after HE staining, the inherent color of red blood cells and the color of eosin changed in the process of staining are observed in an overlapped manner.

Therefore, in a precise sense, the combination of them is referred to as the R dye.

It is generally known that, with regard to a light transmissive substance, the Lambert-beer law represented by the following Equation (7) holds for the relation between the intensity $I_0(\lambda)$ of incident light at each wavelength $\lambda$ and the intensity $I(\lambda)$ of output light.

$$\frac{I(\lambda)}{I_0(\lambda)}=e^{-k(\lambda)d} \quad (7)$$

In Equation (7), $k(\lambda)$ denotes a value unique to a substance, determined depending on a wavelength, and d denotes the thickness of a substance. Here, as the left side of Equation (7) means the spectral transmittance $t(\lambda)$, Equation (7) is replaceable with the following Equation (8).

$$t(\lambda)=e^{-k(\lambda)d} \quad (8)$$

Furthermore, the spectral absorbance $a(\lambda)$ is represented by the following Equation (9).

$$a(\lambda)=k(\lambda)d \quad (9)$$

Thus, Equation (8) is replaceable with the following Equation (10).

$$t(\lambda)=e^{-a(\lambda)} \quad (10)$$

When the stained specimen after HE staining have been stained with three types of dyes, the H dye, the E dye, and the R dye, the following Equation (11) holds according to the Lambert-Beer law with regard to each wavelength $\lambda$.

$$\frac{I(\lambda)}{I_0(\lambda)}=e^{-(k_H(\lambda)d_H+k_E(\lambda)d_E+k_R(\lambda)d_R)} \quad (11)$$

In Equation (11), $k_H(\lambda)$, $k_E(\lambda)$, and $k_R(\lambda)$ represent $k(\lambda)$ that corresponds to the H dye, the E dye, and the R dye, respectively, and they are, for example, the dye spectra (hereafter, referred to as "reference dye spectra") of the respective dyes with which the stained specimen is stained. Furthermore, $d_H$, $d_E$, and $d_R$ represent the virtual thickness of the H dye, the E dye, and the R dye at each sample point corresponding to each pixel location of a multiband image. Naturally, dye is dispersedly present in a stained specimen, and the idea of thickness is not precise; however, it is an index for a relative quantity of dye, indicating how much dye is present, as compared to a case where it is assumed that a stained specimen is stained with a single dye. That is, it can be said that $d_H$, $d_E$, and $d_R$ represent the quantity of dye with regard to the H dye, the E dye, and the R dye, respectively. Furthermore, $k_H(\lambda)$, $k_E(\lambda)$, and $k_R(\lambda)$ may be easily obtained according to the Lambert-Beer law by preparing stained specimens that are individually stained by using the H dye, the E dye, and the R dye, respectively, and measuring the spectral transmittance thereof with a spectroscope.

Here, when the spectral transmittance at the position x is $t(x,\lambda)$ and the spectral absorbance is $a(x,\lambda)$, Equation (9) is replaceable with the following Equation (12).

$$a(x,\lambda)=k_H(\lambda)d_H+k_E(\lambda)d_E+k_R(\lambda)d_R \quad (12)$$

When the estimated spectral transmittance at the wavelength $\lambda$ for the spectral transmittance data $\hat{T}(x)$ estimated by using Equation (5) is $\hat{t}(x,\lambda)$ and the estimated spectral absorbance is $\hat{a}(x,\lambda)$, Equation (12) is replaceable with the following Equation (13). Here, $\hat{t}$ indicates that the symbol "^" is attached to the upper section of t, and $\hat{a}$ indicates that the symbol "^" is attached to the upper section of a.

$$\hat{a}(x,\lambda)=k_H(\lambda)d_H+k_E(\lambda)d_E+k_R(\lambda)d_R \quad (13)$$

In Equation (13), there are three unknown variables, $d_H$, $d_E$, and $d_R$; therefore, they may be solved when simultaneous equations are produced with Equation (13) with regard to at least three different wavelengths $\lambda$. To further increase the accuracy, simultaneous equations may be produced with Equation (13) with regard to four or more different wavelengths $\lambda$ and multiple regression analysis may be conducted. For example, when simultaneous equations are produced with Equation (13) with regard to three wavelengths $\lambda 1$, $\lambda 2$, $\lambda 3$, matrix representation is possible as in the following Equation (14).

$$\begin{pmatrix} \hat{a}(x,\lambda_1) \\ \hat{a}(x,\lambda_2) \\ \hat{a}(x,\lambda_3) \end{pmatrix} = \begin{pmatrix} k_H(\lambda_1) & k_E(\lambda_1) & k_R(\lambda_1) \\ k_H(\lambda_2) & k_E(\lambda_2) & k_R(\lambda_2) \\ k_H(\lambda_3) & k_E(\lambda_3) & k_R(\lambda_3) \end{pmatrix} \begin{pmatrix} d_H \\ d_E \\ d_R \end{pmatrix} \quad (14)$$

Here, Equation (14) is replaceable with the following Equation (15).

$$\hat{A}(x)=Kd(x) \quad (15)$$

In Equation (15), when the number of sample points in the wavelength direction is D, $\hat{A}(x)$ is the matrix in the row D and the column 1 corresponding to $\hat{a}(x,\lambda)$, K is the matrix in the row D and the column 3 corresponding to $k(\lambda)$, and $d(x)$ is the matrix in the row 3 and the column 1 corresponding to $d_H$, $d_E$, and $d_R$ at the point x. Here, $\hat{A}$ indicates that the symbol "^" is attached to the upper section of A.

Furthermore, according to Equation (15), the dye quantities $d_H$, $d_E$, $d_R$ are calculated by using the least squares method. The least squares method is a method for determining $d(x)$ such that the sum of squares of an error is minimized in a single regression analysis equation, and it is calculable with the following Equation (16).

$$\hat{d}(x)=(K^T K)^{-1}K^T \hat{A}(x) \quad (16)$$

In Equation (16), $\hat{d}(x)$ is the estimated quantity of dye. When the estimated dye quantities $\hat{d_H}$, $\hat{d_E}$, $\hat{d_R}$ are substituted into Equation (12), the restored spectral absorbance $\tilde{a}(x,\lambda)$ is obtained with the following Equation (17). Here, $\tilde{a}$ indicates that the symbol "~ (tilde)" is attached to the upper section of a.

$$\tilde{a}(x,\lambda)=k_H(\lambda)\hat{d}_H+k_E(\lambda)\hat{d}_E+k_R(\lambda)\hat{d}_R \quad (17)$$

Thus, the estimated error $e(\lambda)$ for dye-quantity estimation is obtained based on the estimated spectral absorbance $\hat{a}(x,\lambda)$ and the restored spectral absorbance $\tilde{a}(x,\lambda)$ by using the following Equation (18).

$$e(\lambda)=\hat{a}(x,\lambda)-\tilde{a}(x,\lambda) \quad (18)$$

Hereafter, $e(\lambda)$ is described as a residual spectrum. By using Equations (17), (18), the estimated spectral absorbance $\hat{a}(x,\lambda)$ is also representable with the following Equation (19).

$$\hat{a}(x,\lambda)=k_H(\lambda)\hat{d}_H+k_E(\lambda)\hat{d}_E+k_R(\lambda)\hat{d}_R+e(\lambda) \quad (19)$$

After the dye quantities $\hat{d}_H$, $\hat{d}_E$, $\hat{d}_R$ are obtained, they are corrected so that changes in the quantity of dye in the stained specimen may be simulated. Here, the dye quantities $\hat{d}_H$, $\hat{d}_E$ for staining according to a staining method are corrected. The quantity of dye $\hat{d}_R$, which is the inherent color of a red blood cell, is not corrected. That is, the corrected dye quantities $\hat{d}_H^*$, $\hat{d}_E^*$ are obtained by using appropriate coefficients $\alpha_H$, $\alpha_E$ according to the following Equations (20), (21).

$$\hat{d}_H^*=a_H \hat{d}_H \quad (20)$$

$$\hat{d}_E^*=a_E \hat{d}_E \quad (21)$$

By substituting the corrected dye quantities $\hat{d}_H^*$, $\hat{d}_E^*$ into Equation (17), a new restored spectral absorbance $\tilde{a}^*(x,\lambda)$ is obtained by using the following Equation (22).

$$\tilde{a}^*(x,\lambda)=k_H(\lambda)\hat{d}_H^*+k_E(\lambda)\hat{d}_E^*+k_R(\lambda)\hat{d}_R \quad (22)$$

Furthermore, when the residual spectrum $e(\lambda)$ is included, the new estimated spectral absorbance $\hat{a}^*(x,\lambda)$ is obtained by using the following Equation (23).

$$\hat{a}^*(x,\lambda)=k_H(\lambda)\hat{d}_H^*+k_E(\lambda)\hat{d}_E^*+k_R(\lambda)\hat{d}_R+e(\lambda) \quad (23)$$

By substituting the new restored spectral absorbance $\tilde{a}^*(x,\lambda)$ or the new estimated spectral absorbance $\hat{a}^*(x,\lambda)$ into Equation (10), the new spectral transmittance $t^*(x,\lambda)$ is obtained by using the following Equation (24).

$$t^*(\lambda)=e^{-a^*(\lambda)} \quad (24)$$

In Equation (24), the spectral absorbance $a^*(x,\lambda)$ means either the new restored spectral absorbance $\tilde{a}^*(x,\lambda)$ or the new estimated spectral absorbance $\hat{a}^*(x,\lambda)$.

By substituting Equation (24) into Equation (1), the new pixel value $g^*(x,b)$ is obtained by using the following Equation (25). In this case, calculation may be based on zero observed noise $n(b)$.

$$g^*(x,b)=\int_\lambda f(b,\lambda)s(\lambda)e(\lambda)t^*(x,\lambda)d\lambda \quad (25)$$

Here, Equation (25) is replaced with the following Equation (26).

$$G^*(x)=HT^*(x) \quad (26)$$

In Equation (26), $G^*(x)$ is the matrix in the row B and the column 1 corresponding to $g^*(x,b)$, and $T^*(x)$ is the matrix in the row D and the column 1 corresponding to $t^*(x,b)$. Thus, it is possible to compose the pixel value $G^*(x)$ of the stained specimen while the quantity of dye is virtually changed. The above procedure allows virtual adjustment on the quantity of dye in the stained specimen.

The Lambert-Beer law is a formulation of attenuation of light transmitted through a translucent object based on the assumption that there is no refraction or scattering; however, refraction and scattering may occur in the actual stained specimen. Therefore, if attenuation of light due to a stained specimen is modeled by using only the Lambert-Beer law, errors occur due to this modeling. Unfortunately, it is extremely difficult to configure a model including refraction and scattering inside a living body specimen, and it is unexecutable in operation. Therefore, addition of a residual spectrum that is a modeling error including effects of refraction and scattering may prevent unnatural color fluctuation due to a physical model.

Nowadays, there is a disclosed technology of using the above-described Equations (1) to (26) to calculate, from a multiband image of the stained specimen, a single stain image representing the stained state due to the target single staining dye out of staining dyes with which a stained specimen is stained (for example, see Japanese Patent No. 5490568). The staining dyes used are, for example, coloring due to a DAB response (hereafter, referred to as DAB dye) using an EGFR antibody that recognizes an EGFR receptor as well as the above-described H dye and E dye.

Furthermore, according to the technology disclosed in Japanese Patent No. 5490568, a single stain image representing the stained state due to the H dye (hereafter, referred to as H dye-quantity image) is processed with a threshold to extract negative cells, and a single stain image representing the stained state due to the DAB dye (hereafter, referred to as DAB dye-quantity image) is processed with a threshold to extract positive cells, whereby a positive/negative determination may be conducted. Here, an example of the method for extracting cells is a method with which Otsu's method, or the like, is applied to the histogram of pixel values (quantity of dye) of a single stain image to automatically calculate a threshold for binarization so as to extract cells.

SUMMARY

FIG. 18 to FIG. 22 are diagrams that illustrate a conventional problem. Specifically, FIG. 18 is a diagram that illustrates a multiband image (stained-specimen image) 100. Here, in FIG. 18, the darkest part is a positive cell PC that is visualized with the H dye and the DAB dye. Furthermore, the next darkest part is a negative cell NC that is visualized with the H dye. FIG. 19 is a diagram that illustrates a DAB dye-quantity image 200 calculated from the multiband image 100 illustrated in FIG. 18. In the illustration of FIG. 19, a part closer to white has a larger quantity of DAB dye. FIG. 20 is a diagram that illustrates an H dye-quantity image 300 calculated from the multiband image 100 illustrated in FIG. 18. In the illustration of FIG. 20, a part closer to white has a larger quantity of H dye. FIG. 21 is a diagram that illustrates the histogram of pixel values (quantity of dye) of the H dye-quantity image 300. In FIG. 21, the horizontal axis indicates a quantity of dye, and the vertical axis indicates a frequency. (a) of FIG. 21 illustrates the histogram of the entire H dye-quantity image 300. (b) of FIG. 21 is the histogram of pixel values (quantity of dye) in only a partial range (0.01 to 0.1), extracted from the histogram illustrated in (a) of FIG. 21. (c) of FIG. 21 is the histogram of pixel values (quantity of dye) in only a partial range (0.1 to 2), extracted from the histogram illustrated in (a) of FIG. 21. FIG. 22 is a diagram that illustrates an image 400 after Otsu's method, or the like, is applied to the histogram illustrated in FIG. 21 to automatically calculate a threshold for binarization and an H stained area ArH' (part illustrated in white) due to the H dye is extracted.

When there are a small number of bands in a multiband image, little information causes a decrease in the accuracy of a calculated single stain image. For example, when cell nucleus immunostain for visualizing the positive cell PC with the DAB dye and cell nucleus counterstain for visualizing the negative cell NC with the H dye are applied to the stained specimen, the H dye tends to be excessively detected on an area of the positive cell PC of the H dye-quantity image 300 (FIG. 18 to FIG. 20). That is, artifacts occur in a range of a high quantity of dye in the histogram of pixel values (quantity of dye) of the H dye-quantity image 300 (FIG. 21). Therefore, when a threshold is automatically calculated by applying Otsu's method, or the like, to the histogram of pixel values of the H dye-quantity image 300, artifacts present in the histogram make it difficult to calculate a desirable threshold. As a result, as it is understood from the comparison between the multiband image 100 illustrated in FIG. 18 or the DAB dye-quantity image 200 illustrated in FIG. 19 and the H stained area ArH' illustrated in FIG. 22, there is a problem in that the positive cell PC is sometimes extracted as the negative cell NC and it is difficult to extract cells in a desirable manner.

In some embodiments, an image processing device includes a processor including hardware. The processor is configured to: calculate each single stain image representing a stained state due to each stain from a stained-specimen image that has captured a specimen to which at least two types of stains are applied; sequentially perform, on all the at least two types of stains, an extraction process to extract a stained area due to a target stain from the single stain image of the target stain, starting from a stain having high specificity with regard to a target site; sequentially perform a correction process, on all at least one type of second stain except for a first stain having the highest specificity among the at least two types of stains, to correct the single stain image by excluding stained areas of all stains having higher specificity than the target stain from the single stain image of the target stain, starting from the stain having the high specificity; extract the stained area due to the target stain from a corrected single stain image that is obtained after the correction process is performed on the single stain image of the target stain, to extract the stained area due to the second stain; and analyze an image based on the stained area.

In some embodiments, an image processing method includes: calculating each single stain image representing a stained state due to each stain from a stained-specimen image that has captured a specimen to which at least two types of stains are applied; sequentially performing, on all the at least two types of stains, an extraction process to extract a stained area due to a target stain from the single stain image of the target stain, starting from a stain having high specificity with regard to a target site; sequentially performing a correction process, on all at least one type of second stain except for a first stain having the highest specificity among the at least two types of stains, to correct the single stain image by excluding stained areas of all stains having higher specificity than the target stain from the single stain image of the target stain, starting from the stain having the high specificity; extracting the stained area due to the target stain from a corrected single stain image that is obtained after the correction process is performed on the single stain image of the target stain, to extract the stained area due to the second stain; and analyzing an image based on the stained area.

In some embodiments, a non-transitory computer-readable recording medium recording an image processing program causing an image processing device to implement the image processing method.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
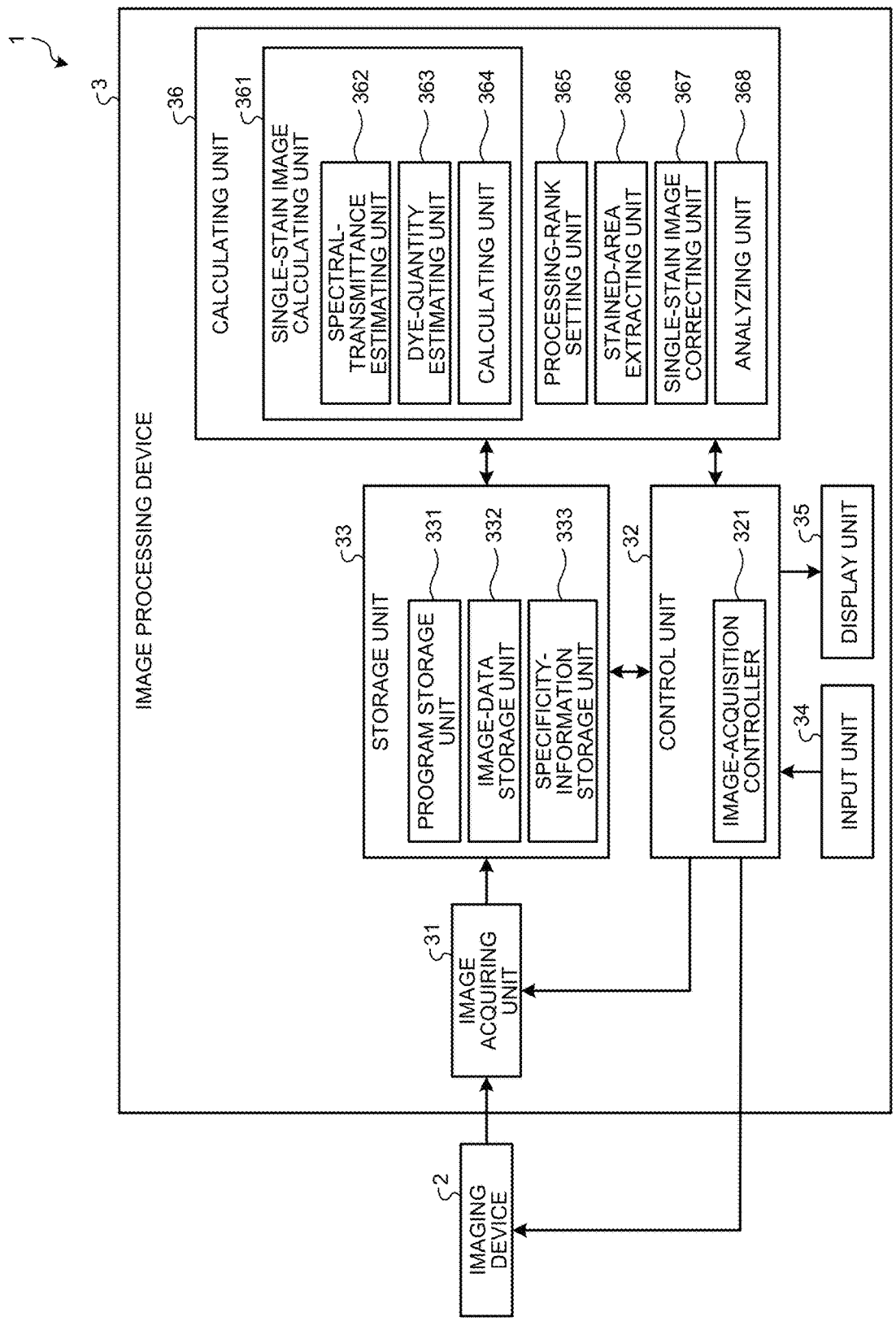
FIG. 1 is a block diagram that illustrates a configuration of an imaging system according to a first embodiment.

With reference to drawings, an explanation is given below of an aspect (hereafter, referred to as "embodiment") for implementing the disclosure. Furthermore, the disclosure is not limited to the embodiment described below. Moreover, in description of drawings, the same components are attached with the same reference numeral.

First Embodiment

Schematic Configuration of an Imaging System

FIG. 1 is a block diagram that illustrates a configuration of an imaging system 1 according to the first embodiment.

The imaging system 1 is a system that captures a stained specimen to which at least two types of stains have been applied and that processes a stained-specimen image during capturing.

Here, at least two types of stains applied to a stained specimen may be, for example, cell nucleus immunostain using Ki-67, ER, PgR, or the like, as an antibody, cell membrane immunostain using HER2, or the like, as an antibody, cytoplasmic immunostain using serotonin, or the like, as an antibody, cell nucleus counterstain using hematoxylin (H) as a dye, or cytoplasmic counterstain using eosin (E) as a dye.

Furthermore, as illustrated in FIG. 1, the imaging system 1 includes an imaging device 2 and an image processing device 3.

Configuration of the Imaging Device

Figure 2:
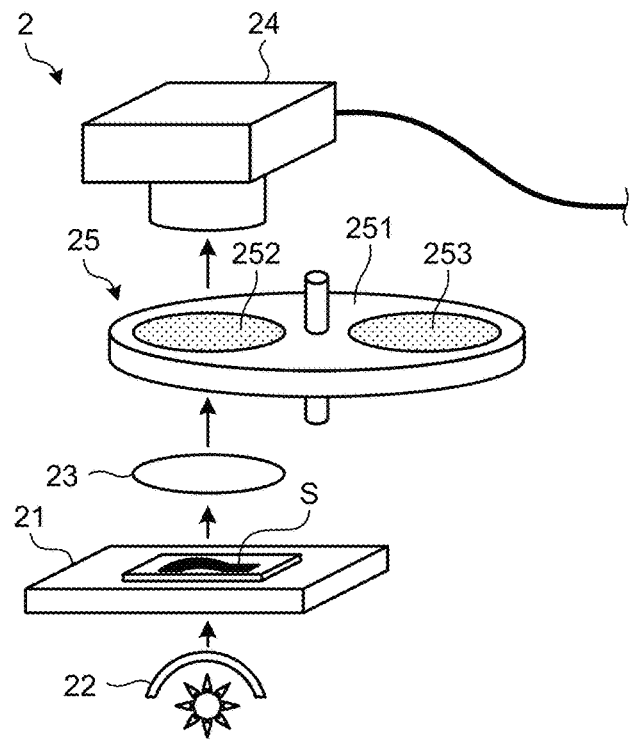
FIG. 2 is a diagram that schematically illustrates a configuration of an imaging device illustrated in FIG. 1.

FIG. 2 is a diagram that schematically illustrates a configuration of the imaging device 2.

The imaging device 2 is a device that acquires a multiband image (an equivalence of the stained-specimen image according to the disclosure) of a stained specimen S to which at least two types of stains have been applied. As illustrated in FIG. 2, the imaging device 2 includes a stage 21, an illumination unit 22, a tube lens 23, an RGB camera 24, and a filter unit 25.

The stage 21 is a section on which the stained specimen S is placed, and it is configured to move under the control of the image processing device 3 so as to change the observed area of the stained specimen S.

The illumination unit 22 emits illumination light to the stained specimen S placed on the stage 21 under the control of the image processing device 3.

The tube lens 23 focuses transmitted light, which has been emitted to the stained specimen S and passed through the stained specimen S, to the RGB camera 24.

Figure 3:
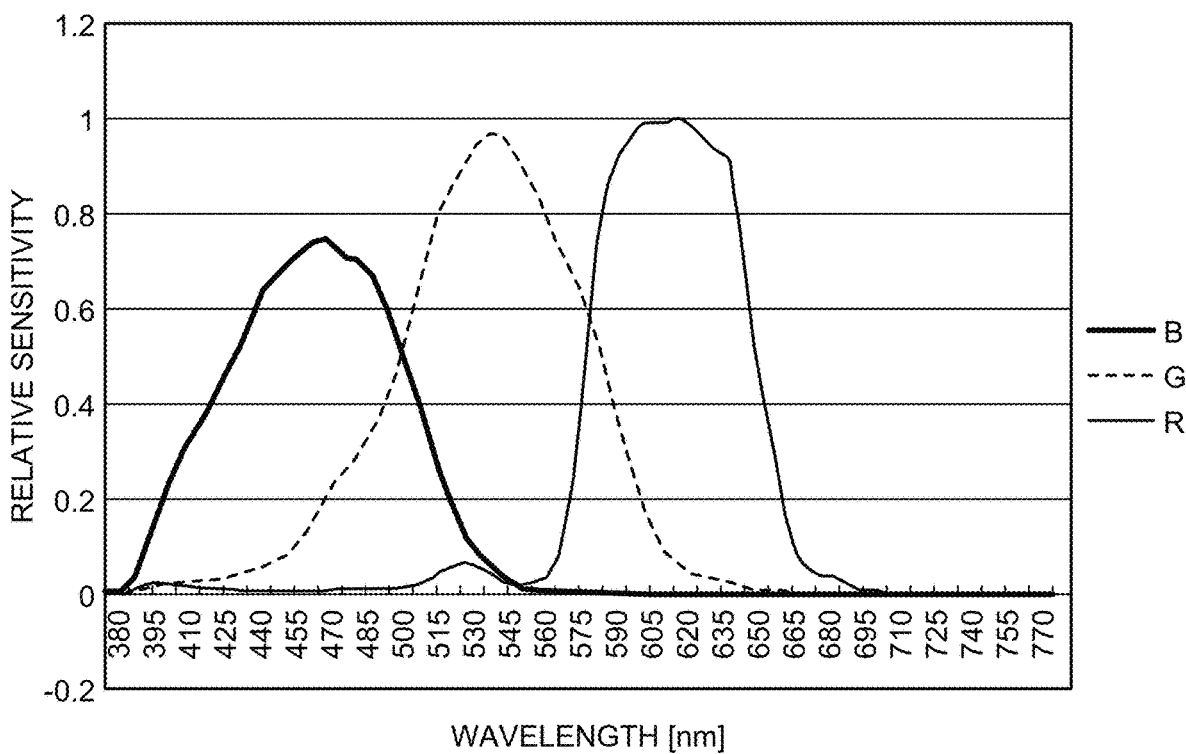
FIG. 3 is a diagram that illustrates an example of the spectral sensitivity property of an RGB camera illustrated in FIG. 2.

FIG. 3 is a diagram that illustrates an example of the spectral sensitivity property of the RGB camera 24.

The RGB camera 24 includes an imaging element such as CCD (Charge Coupled Device) or CMOS (Complementary Metal Oxide Semiconductor), and it captures transmitted light having passed through the stained specimen S under the control of the image processing device 3. For example, the RGB camera 24 has spectral sensitivity properties of respective R (red), G (green), and B (blue) bands illustrated in FIG. 3.

Figure 4:
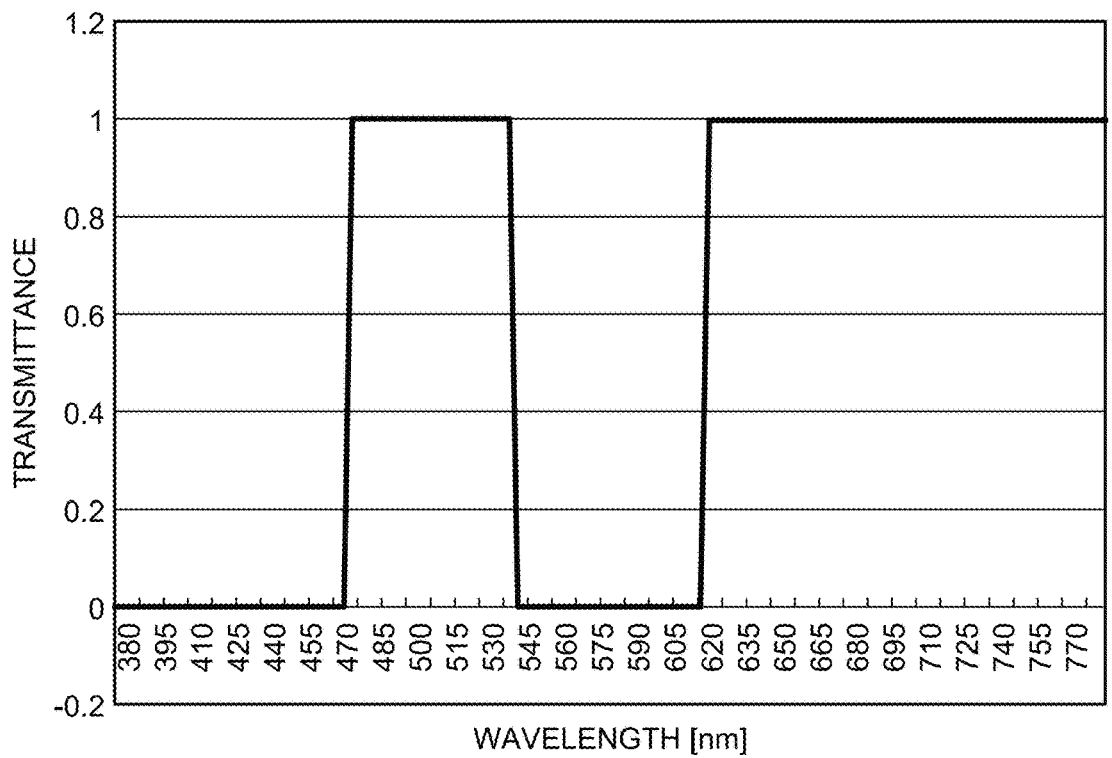
FIG. 4 is a diagram that illustrates an example of the spectral property of a first filter illustrated in FIG. 2.
Figure 5:
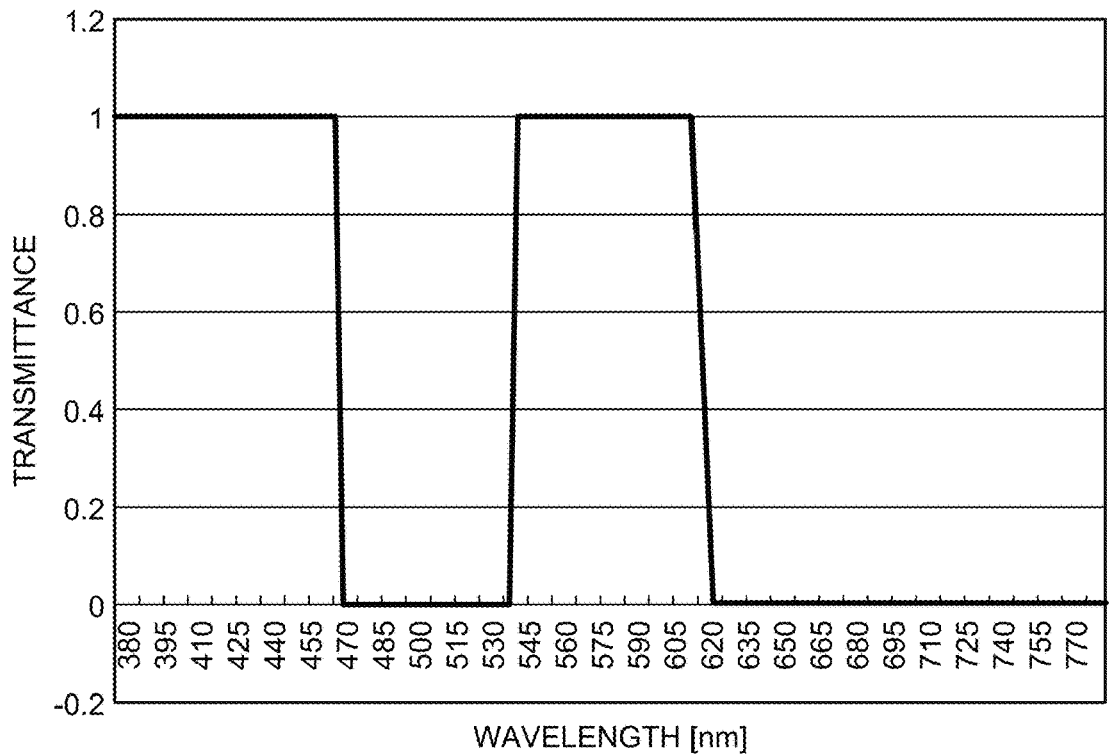
FIG. 5 is a diagram that illustrates an example of the spectral property of a second filter illustrated in FIG. 2.

FIG. 4 is a diagram that illustrates an example of the spectral property of a first filter 252. FIG. 5 is a diagram that illustrates an example of the spectral property of a second filter 253.

The filter unit 25 is disposed on the optical path leading from the tube lens 23 to the RGB camera 24, and it limits the wavelength band of light focused on the RGB camera 24 to a predetermined range. The filter unit 25 includes: a filter wheel 251 that is rotatable under the control of the image processing device 3; and the first and the second filters 252, 253 provided on the filter wheel 251 and having different spectral properties (e.g., the spectral properties in FIG. 4, FIG. 5) to divide a transparent wavelength region of each R, G, B band into two.

Furthermore, the imaging device 2 acquires a multiband image of the stained specimen S under the control of the image processing device 3 as described below.

First, the imaging device 2 locates the first filter 252 on the optical path leading from the illumination unit 22 to the RGB camera 24 and emits illumination light from the illumination unit 22 to the stained specimen S. Then, the RGB camera 24 captures (first capturing) the transmitted light, which has been transmitted through the stained specimen S and passed through the first filter 252 and the tube lens 23.

Then, the imaging device 2 locates the second filter 253 on the optical path leading from the illumination unit 22 to the RGB camera 24 and conducts second capturing in the same manner as the first capturing.

Thus, different images in three bands are acquired during the first and the second capturings so that multiband images in the total of six bands are acquired.

Here, the number of filters provided in the filter unit 25 may be not only two but also equal to or more than three to acquire images in more bands. Furthermore, the imaging device 2 may be configured not to include the filter unit 25 so as to acquire only RGB images by using the RGB camera 24. Furthermore, instead of the filter unit 25, it is possible to adopt a liquid crystal tunable filter or an acousto-optical tunable filter that is capable of changing the spectral property. Moreover, multiband images may be acquired by switching lights having different spectral properties and emitting them to the stained specimen S.

Configuration of the Image Processing Device

The image processing device 3 is a device that processes multiband images of the stained specimen S acquired by the imaging device 2. As illustrated in FIG. 1, the image processing device 3 includes an image acquiring unit 31, a control unit 32, a storage unit 33, an input unit 34, a display unit 35, and a calculating unit 36.

The image acquiring unit 31 is configured as appropriate in accordance with the configuration of the imaging system 1. For example, when the imaging device 2 is connected to the image processing device 3, the image acquiring unit 31 is configured by using an interface that loads multiband images (image data) output from the imaging device 2. Furthermore, when a server is installed to store multiband images acquired by the imaging device 2, the image acquiring unit 31 is configured by using a communication device, or the like, connected to the server so as to conduct data communications with the server and acquire multiband images. Alternatively, the image acquiring unit 31 may be configured by using a reader to which a portable recording medium is removably attached and which reads multiband images stored in the recording medium.

The control unit 32 is configured by using a CPU (Central Processing Unit), or the like. The control unit 32 includes an image-acquisition controller 321 that controls operations of the image acquiring unit 31 and the imaging device 2 to acquire multiband images. Furthermore, the control unit 32 controls operations of the image acquiring unit 31 and the imaging device 2 on the basis of input signals input from the input unit 34, multiband images input from the image acquiring unit 31, and programs and data stored in the storage unit 33.

The storage unit 33 is configured by using various IC memories, e.g., ROM (Read Only Memory) such as flash memory that is updatable and recordable, or RAM (Random Access Memory), a hard disk that is built in or connected via a data communication terminal, or an information storage device such as CD-ROM, and an information writing/reading device for the information storage device, or the like. As illustrated in FIG. 1, the storage unit 33 includes: a program storage unit 331 that stores an image processing program; an image-data storage unit 332 that stores multiband images acquired by the image acquiring unit 31 and image data, various parameters, and the like, used when the image processing program is executed; and a specificity-information storage unit 333 that stores specificity information illustrated in, for example, Table 1 described below.

The specificity information is information used for setting a processing rank during an extraction process and a correction process, described later, by the calculating unit 36, and it is information in which stains are sequentially ranked, starting from the stain having the highest specificity (the highest binding power) with regard to the target site, which is targeted for staining. Specifically, in the specificity information, as illustrated in Table 1, cell nucleus immunostain ranks at the top, and cell membrane immunostain, cytoplasmic immunostain, cell nucleus counterstain, and cytoplasmic counterstain are set to be lower sequentially in rank. Here, the following Table 1 is an example, and the rank is changed depending on an individually produced antibody. For example, it is determined, depending on the produced antibody, that serotonin ranks first and Ki-67 ranks third.

TABLE 1

| Rank | Types of stains (antibody or dye) |
|---|---|
| 1 | Cell nucleus immunostain (Ki-67, ER, PgR) |
| 2 | cell membrane immunostain (HER2) |
| 3 | cytoplasmic immunostain (serotonin) |
| 4 | cell nucleus counterstain (H) |
| 5 | cytoplasmic counterstain (E) |

Hereafter, among at least two types of stains applied to the stained specimen S, the stain that ranks at the top (the highest specificity) is described as a first stain, and the other stains as second stains.

The input unit 34 is configured by using various types of input devices such as keyboard, mouse, touch panel, or various switches, and it outputs input signals corresponding to operation input to the control unit 32. For example, the input unit 34 takes input of the type of stain applied to the stained specimen S in accordance with a user operation. Then, the control unit 32 adds, as metadata, information indicating the input type of stain to a multiband image stored in the image-data storage unit 332.

The display unit 35 is implemented by using a display device such as LCD (Liquid Crystal Display), EL (Electro Luminescence) display, or CRT (Cathode Ray Tube) display, and it displays various types of screens based on display signals input from the control unit 32.

The calculating unit 36 is configured by using a CPU, or the like. The calculating unit 36 reads a multiband image stored in the image-data storage unit 332 and recognizes the type of stain applied to the stained specimen S based on the metadata added to the multiband image. Then, the calculating unit 36 executes image processing on the multiband image in accordance with each recognized stain. As illustrated in FIG. 1, the calculating unit 36 includes a single-stain image calculating unit 361, a processing-rank setting unit 365, a stained-area extracting unit 366, a single-stain image correcting unit 367, and an analyzing unit 368.

The single-stain image calculating unit 361 calculates single stain images each representing a stained state due to each stain from the multiband image. As illustrated in FIG. 1, the single-stain image calculating unit 361 includes a spectral-transmittance estimating unit 362, a dye-quantity estimating unit 363, and a calculating unit 364.

The spectral-transmittance estimating unit 362 estimates the spectral transmittance of each pixel from the multiband image.

The dye-quantity estimating unit 363 estimates the quantity of dye in each pixel with regard to each stain by using the spectral transmittance estimated by the spectral-transmittance estimating unit 362.

The calculating unit 364 calculates a single stain image of each of the stains based on the quantity of dye in each pixel with regard to each stain, estimated by the dye-quantity estimating unit 363.

The processing-rank setting unit 365 sets the processing rank of each stain applied to the stained specimen S during an extraction process of the stained-area extracting unit 366 and a correction process of the single-stain image correcting unit 367 based on the specificity information stored in the specificity-information storage unit 333.

The stained-area extracting unit 366 performs a process to extract a stained area due to the target stain from a single stain image of the target stain with every stain applied to the stained specimen S in accordance with the processing rank set by the processing-rank setting unit 365. Furthermore, to extract a stained area due to the second stain, the stained-area extracting unit 366 extracts a stained area due to the target stain from a corrected single stain image that is obtained after the single-stain image correcting unit 367 performs a correction process on the single stain image of the target stain.

The single-stain image correcting unit 367 performs, on all the second stains in accordance with the processing rank, a correction process to correct the single stain image by excluding, from the single stain image of the target stain, stained areas of all the stains that rank higher than the target stain in the processing rank set by the processing-rank setting unit 365.

The analyzing unit 368 analyzes an image based on a stained area extracted by the stained-area extracting unit 366.

Operation of the Imaging System

Next, operation of the above-described imaging system 1 is explained.

Figure 6:
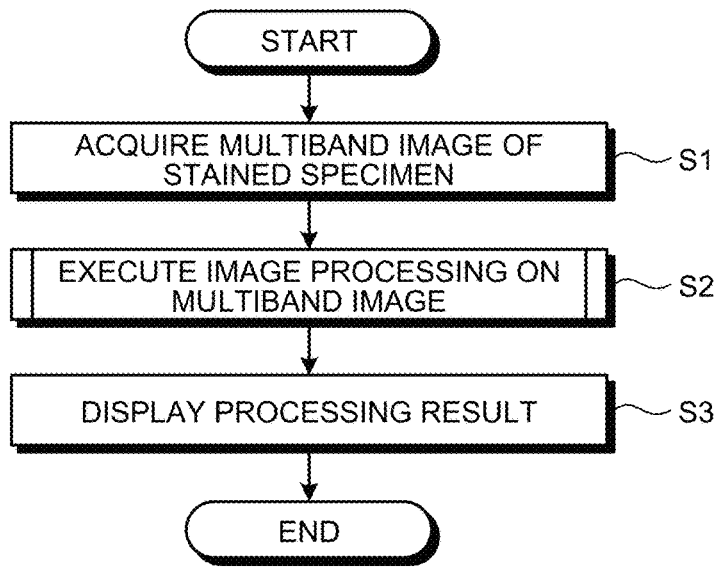
FIG. 6 is a flowchart that illustrates operation of the imaging system illustrated in FIG. 1.

FIG. 6 is a flowchart that illustrates operation of the imaging system 1.

First, the image-acquisition controller 321 controls operation of the imaging device 2 so as to acquire a multiband image of the stained specimen S (Step S). The multiband image acquired by the imaging device 2 is stored in the storage unit 33 (the image-data storage unit 332) via the image acquiring unit 31.

Figure 18:
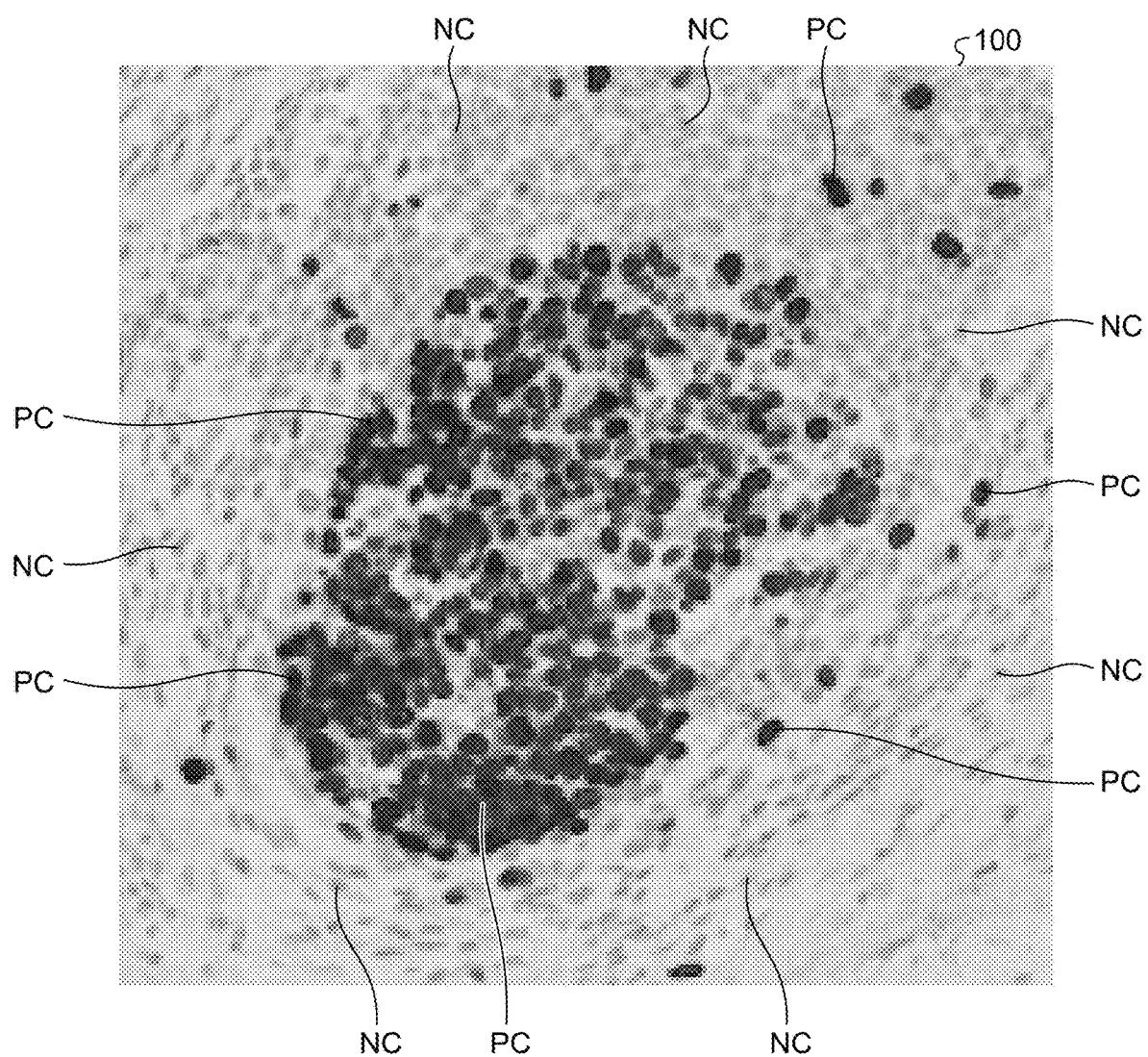
FIG. 18 is a diagram that illustrates a conventional problem.

It is assumed below that two types of stains, cell nucleus immunostain and cell nucleus counterstain, have been applied to the stained specimen S. That is, for example, as illustrated in FIG. 18, on a multiband image 100 acquired by the imaging device 2, the positive cell PC and the negative cell NC are visualized by the DAB dye and the H dye, respectively. For the convenience of the following explanation, the cell nucleus immunostain is described as DAB stain, and the cell nucleus counterstain as H stain.

After Step S1, the calculating unit 36 reads the multiband image 100 stored in the image-data storage unit 332 and recognizes the type of stains (here, the DAB stain and the H stain) applied to the stained specimen S based on the metadata attached to the multiband image 100. Then, the calculating unit 36 executes image processing on the multiband image 100 in accordance with each recognized stain (Step S2).

Figure 7:
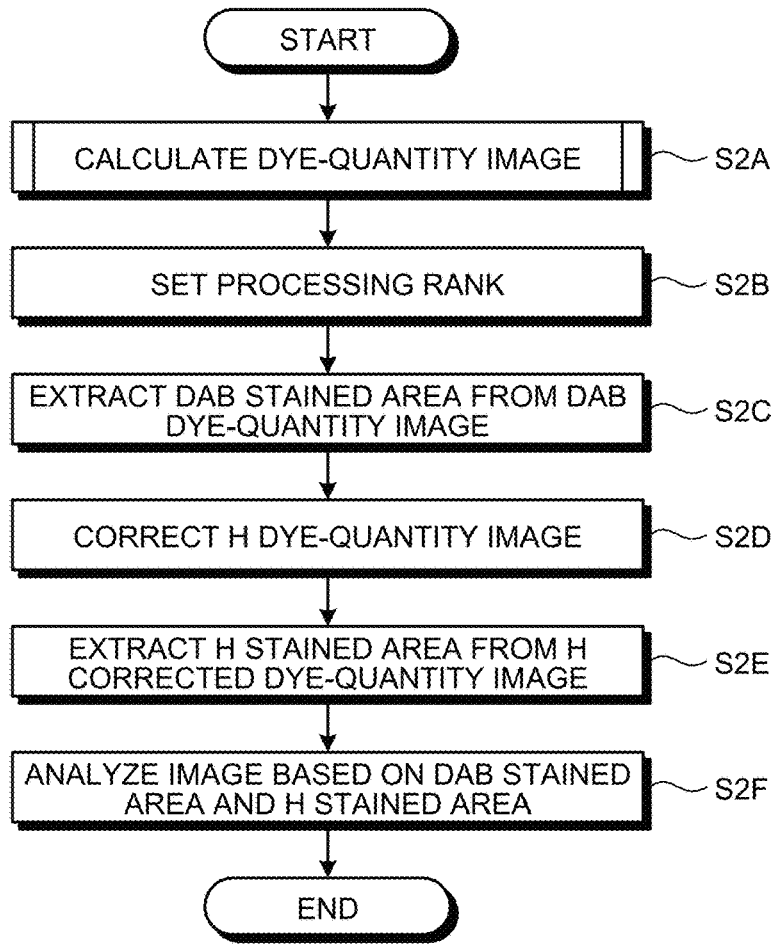
FIG. 7 is a flowchart that illustrates the procedure at Step S2 illustrated in FIG. 6.

FIG. 7 is a flowchart that illustrates the procedure at Step S2. Here, the flowchart illustrated in FIG. 7 is equivalent to the image processing method according to the disclosure.

The single-stain image calculating unit 361 calculates single stain images each representing the stained state of each of the stains, the DAB stain and the H stain, from the multiband image 100 (Step S2A: a single-stain image calculation step).

Here, according to the first embodiment, the single-stain image calculating unit 361 calculates, as a single stain image, a dye-quantity image in which a pixel value is a quantity of dye.

Figure 8:
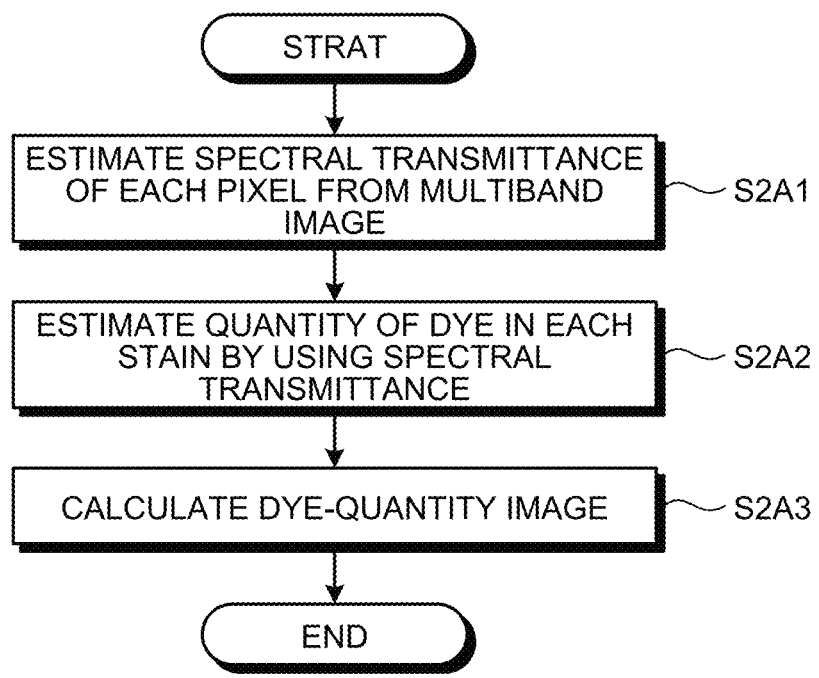
FIG. 8 is a flowchart that illustrates the procedure of a single-stain image calculation step S2A illustrated in FIG. 7.

FIG. 8 is a flowchart that illustrates the procedure of the single-stain image calculation step S2A.

The spectral-transmittance estimating unit 362 estimates the spectral transmittance of each pixel from the multiband image 100 by using for example Wiener estimation (the above-described Equations (1) to (6)) (Step S2A1).

After Step S2A1, the dye-quantity estimating unit 363 estimates the quantity of dye in each pixel with regard to each of the stains, the DAB stain and the H stain, by using the spectral transmittance estimated by the spectral-transmittance estimating unit 362 according to for example the Lambert-Beer law (the above-described Equations (7) to (16)) (Step S2A2).

Figure 19:
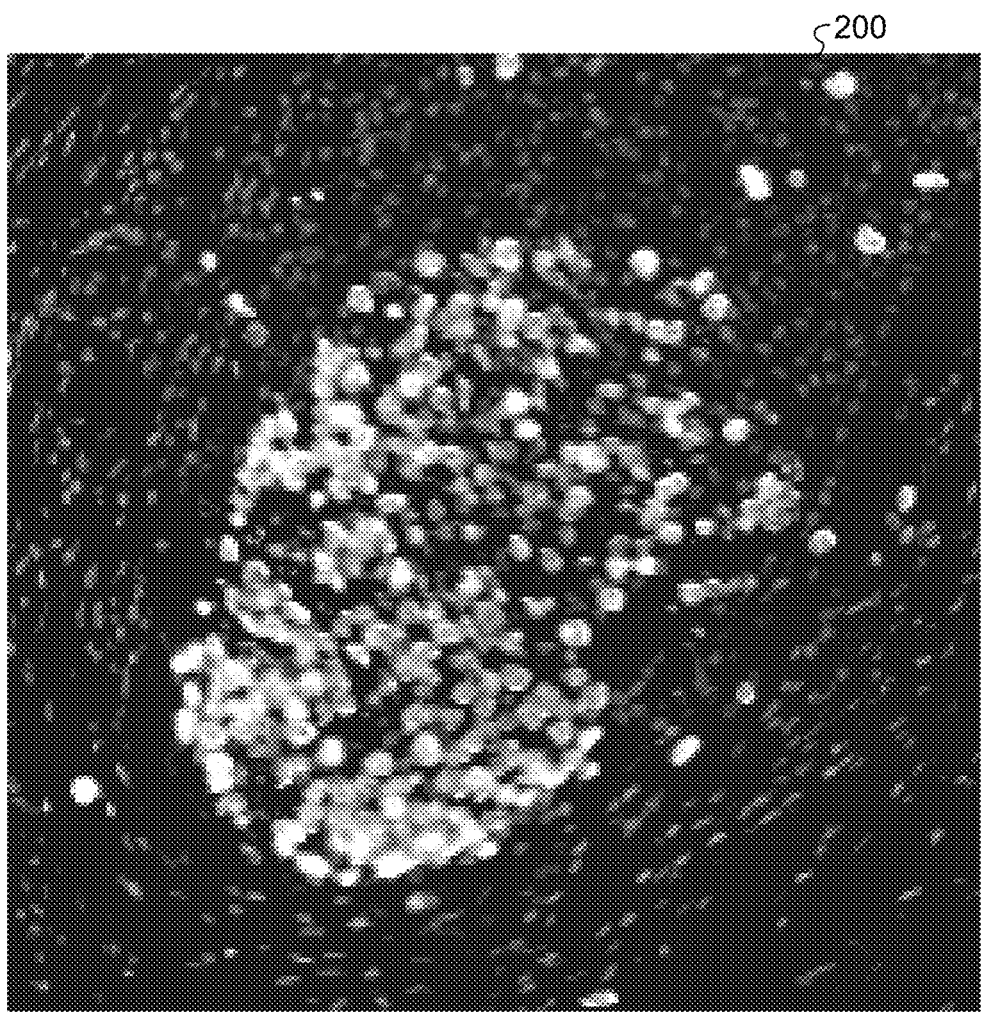
FIG. 19 is a diagram that illustrates a conventional problem.
Figure 20:
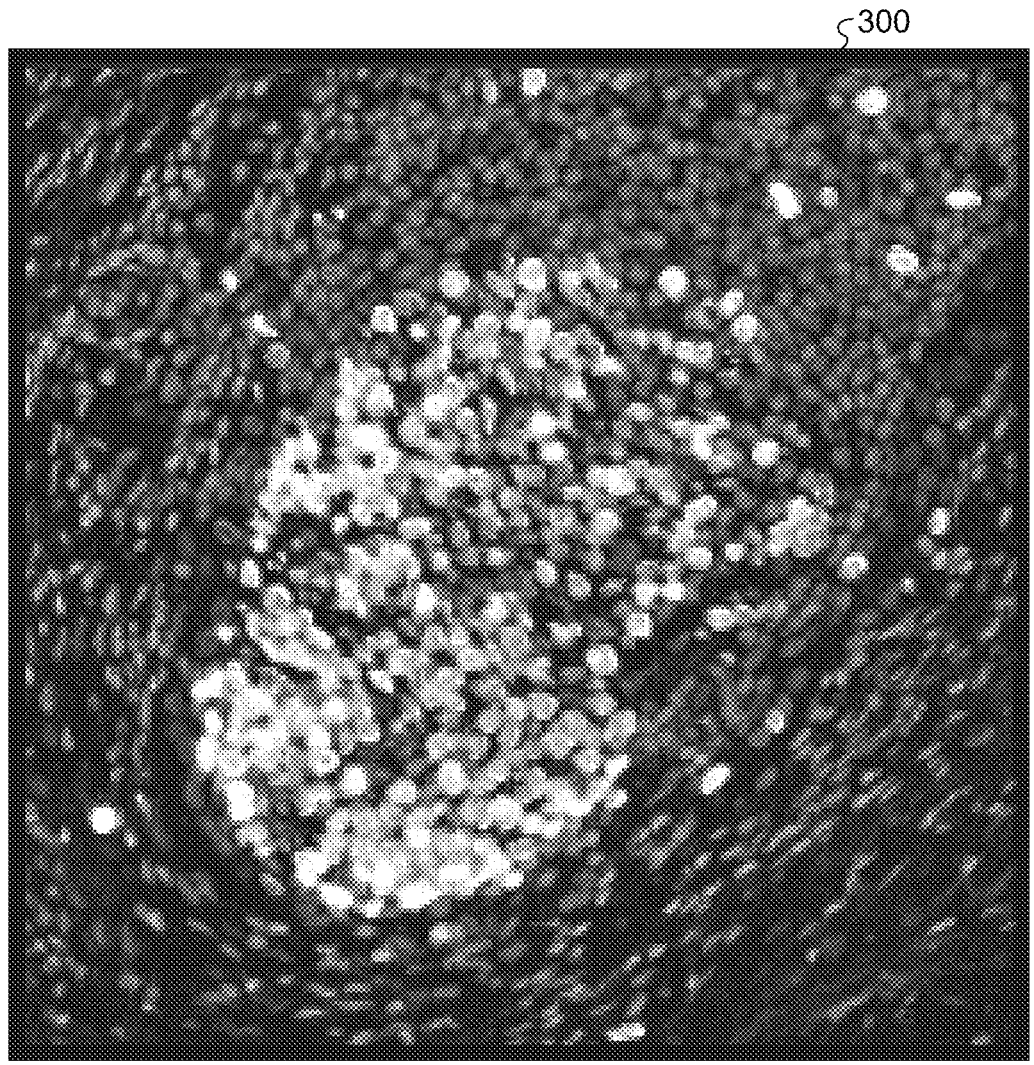
FIG. 20 is a diagram that illustrates a conventional problem.

After Step S2A2, the calculating unit 364 calculates the DAB dye-quantity image 200 (FIG. 19) in which each pixel value is the quantity of dye in each pixel with regard to the DAB stain, estimated by the dye-quantity estimating unit 363, and the H dye-quantity image 300 (FIG. 20) in which each pixel value is the quantity of dye in each pixel with regard to the H stain, estimated by the dye-quantity estimating unit 363 (Step S2A3).

After Step S2A, the processing-rank setting unit 365 sets the processing ranks of the DAB stain and the H stain based on specificity information stored in the specificity-information storage unit 333 (Step S2B). Specifically, at Step S2B, the processing-rank setting unit 365 sets the first processing rank to the DAB stain (the first stain) and the second processing rank to the H stain (the second stain).

After Step S2B, the stained-area extracting unit 366 performs an extraction process to extract a DAB stained area due to the DAB stain (the first stain), which is set as the first processing rank by the processing-rank setting unit 365, from the DAB dye-quantity image 200 of the DAB stain (Step S2C: a stained-area extraction step).

Figure 9:
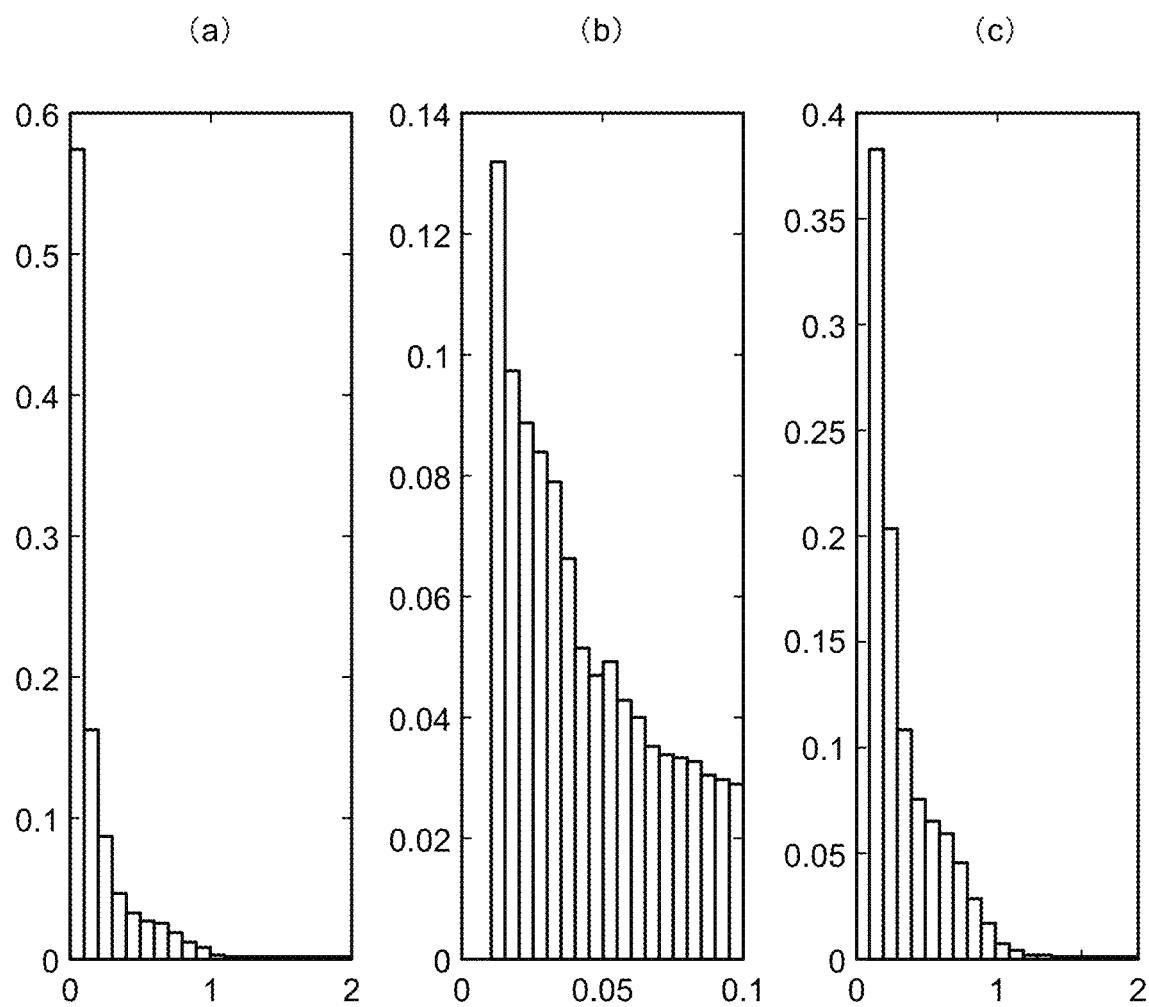
FIG. 9 is a diagram that illustrates an example of the histogram of pixel values of a DAB dye-quantity image calculated at a stained-area extraction step S2C illustrated in FIG. 7.
Figure 10:
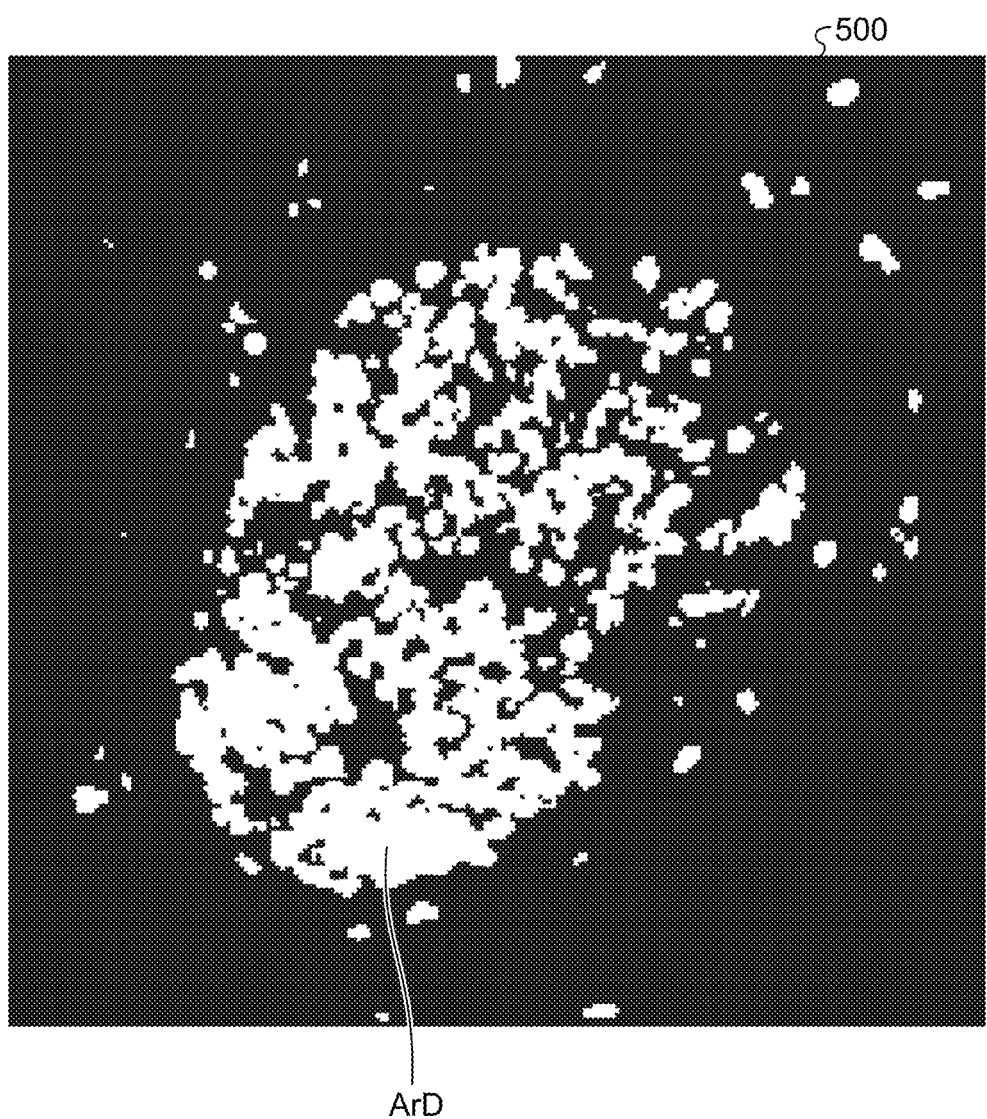
FIG. 10 is a diagram that illustrates an example of an image of DAB stained areas extracted at the stained-area extraction step S2C illustrated in FIG. 7.

FIG. 9 is a diagram that illustrates an example of the histogram of pixel values of the DAB dye-quantity image 200 calculated at the stained-area extraction step S2C. Here, (a) to (c) of FIG. 9 are histograms corresponding to (a) to (c) of FIG. 21. FIG. 10 is a diagram that illustrates an example of an image 500 of DAB stained areas ArD (portions illustrated in white) extracted at the stained-area extraction step S2C.

Specifically, at Step S2C, the stained-area extracting unit 366 calculates the histogram (FIG. 9) of pixel values of the DAB dye-quantity image 200. Then, the stained-area extracting unit 366 applies Otsu's method, K-means algorithm, or the like, to the calculated histogram to automatically calculate a threshold for binarization and then extracts the DAB stained area ArD (FIG. 10) due to the DAB stain.

Figure 11:
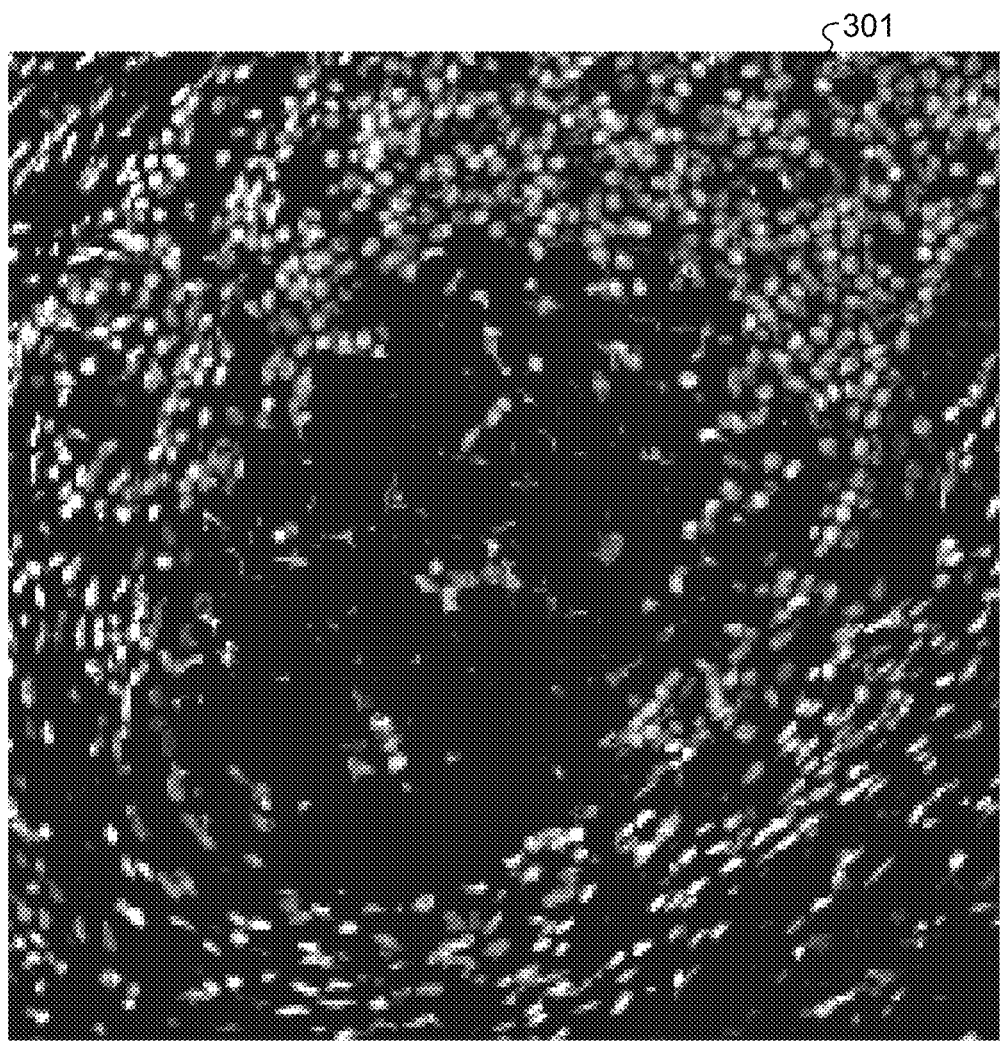
FIG. 11 is a diagram that illustrates an example of an H corrected dye-quantity image calculated at a single-stain image correction step S2D illustrated in FIG. 7.

FIG. 11 is a diagram that illustrates an example of an H corrected dye-quantity image 301 calculated at a single-stain image correction step S2D. In the illustration of FIG. 11, a part closer to white has a larger quantity of H dye.

After Step S2C, the single-stain image correcting unit 367 calculates the H corrected dye-quantity image 301 (FIG. 11)

that is obtained after the H dye-quantity image 300 of the H stain (the second stain) that is set as the second processing rank by the processing-rank setting unit 365 is corrected by excluding, from the H dye-quantity image 300, the DAB stained area ArD of the DAB stain (the first stain) that is set as the first processing rank by the processing-rank setting unit 365 (Step S2D: a single-stain image correction step).

Moreover, the DAB stained area ArD excluded from the H corrected dye-quantity image 301 is a portion that is not the processing target for the subsequent process (Step S2E).

After Step S2D, the stained-area extracting unit 366 performs an extraction process to extract an H stained area due to the H stain (the second stain), which is set as the second processing rank by the processing-rank setting unit 365, from the H corrected dye-quantity image 301 of the H stain (Step S2E: a stained-area extraction step).

Figure 12:
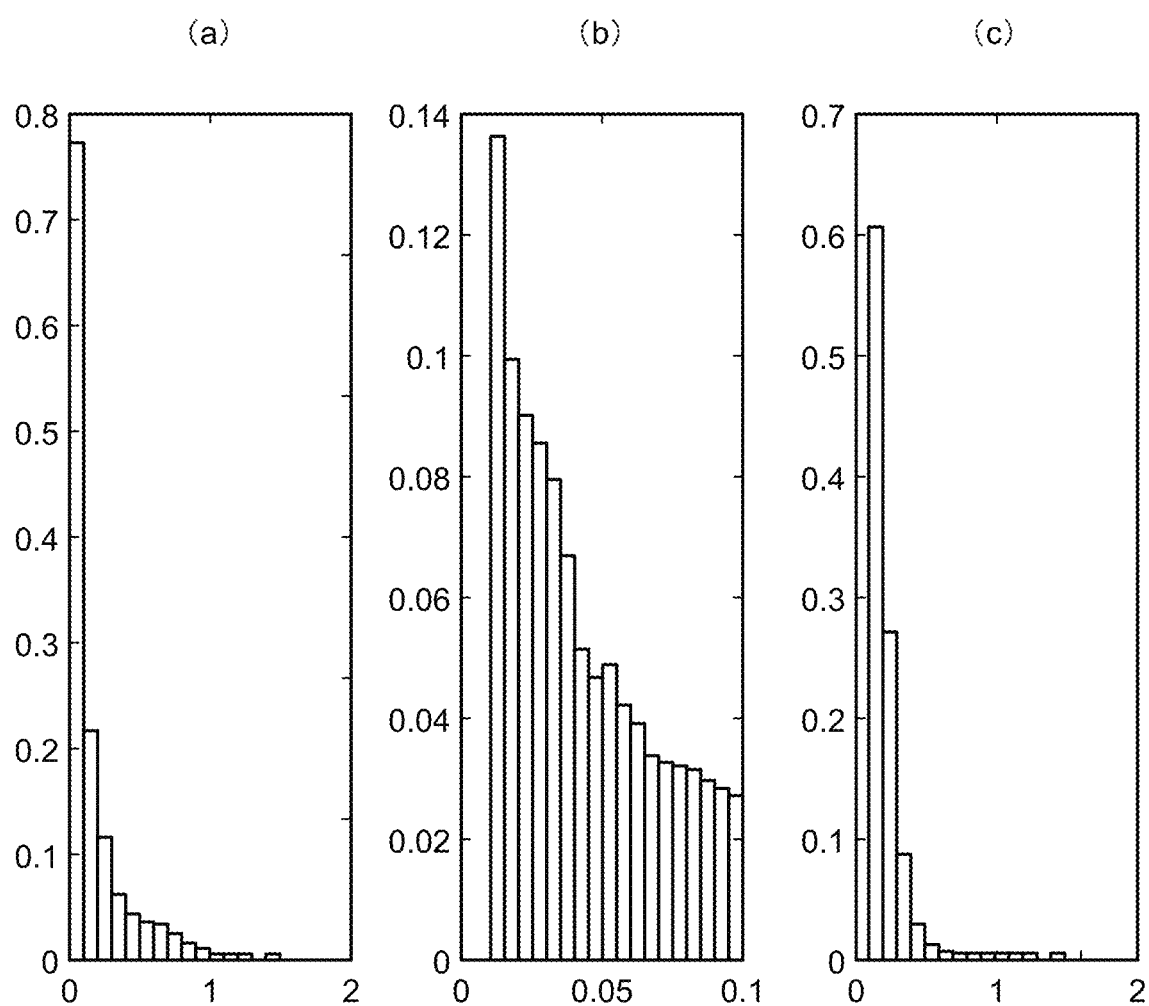
FIG. 12 is a diagram that illustrates an example of the histogram of pixel values of an H corrected dye-quantity image calculated at a stained-area extraction step S2E illustrated in FIG. 7.
Figure 13:
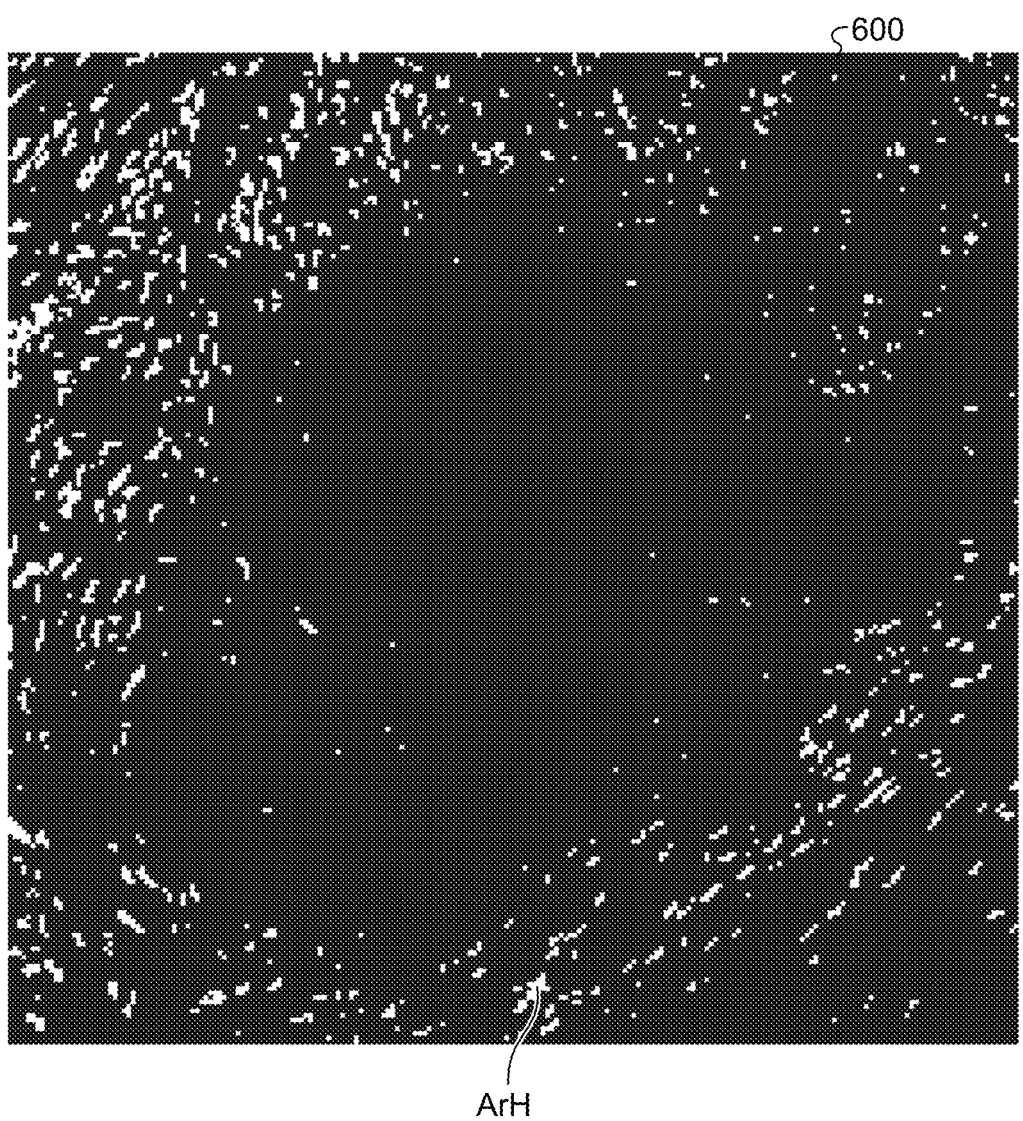
FIG. 13 is a diagram that illustrates an example of an image of H stained areas extracted at the stained-area extraction step S2E illustrated in FIG. 7.

FIG. 12 is a diagram that illustrates an example of the histogram of pixel values of the H corrected dye-quantity image 301 calculated at a stained-area extraction step S2E. Here, (a) to (c) of FIG. 12 are histograms corresponding to (a) to (c) of FIG. 21. FIG. 13 is a diagram that illustrates an example of an image 600 of H stained areas ArH (portions illustrated in white) extracted at the stained-area extraction step S2E.

Specifically, at Step S2E, the stained-area extracting unit 366 calculates the histogram (FIG. 12) of pixel values of the H corrected dye-quantity image 301. Then, the stained-area extracting unit 366 applies Otsu's method, K-means algorithm, or the like, to the calculated histogram to automatically calculate a threshold for binarization and then extracts the H stained area ArH (FIG. 13) of the H stain.

After Step S2E, the analyzing unit 368 analyzes the image based on the DAB stained area ArD and the H stained area ArH (Step S2F: an analysis step).

For example, at Step S2F, the analyzing unit 368 performs morphology processing such as expansion, contraction, or compensation, on the DAB stained area ArD to correct the shape of positive cells and counts the positive cells. Furthermore, the analyzing unit 368 performs the above-described morphology processing on the H stained area ArH to correct the shape of negative cells and counts the negative cells. Then, the analyzing unit 368 makes a positive/negative determination.

After Step S2, the control unit 32 causes the display unit 35 to display processing results (images representing the DAB stained area ArD and the H stained area ArH, the count values of positive cells and negative cells, a result of positive/negative determination, and the like) obtained by the calculating unit 36 (Step S3).

The first embodiment described above produces the following advantages.

The image processing device 3 according to the first embodiment sequentially performs an extraction process to extract a stained area due to the target stain from the target dye-quantity image with regard to every stain applied to the stained specimen S, starting from the stain having high specificity. Furthermore, the image processing device 3 sequentially performs a correction process, on all of the second stains in at least one type except for the first stain having the highest specificity among the stains applied to the stained specimen S, to correct the dye-quantity image of the target stain by excluding stained areas of all the stains having higher specificity than the target stain from the dye-quantity image, starting from the stain having the highest specificity. Furthermore, to extract a stained area due to the second stain, the image processing device 3 extracts a stained area due to the target stain from the corrected single stain image that is obtained after the correction process is performed on the dye-quantity image of the target stain. Then, the image processing device 3 analyzes the image based on the extracted stained area.

Figure 21:
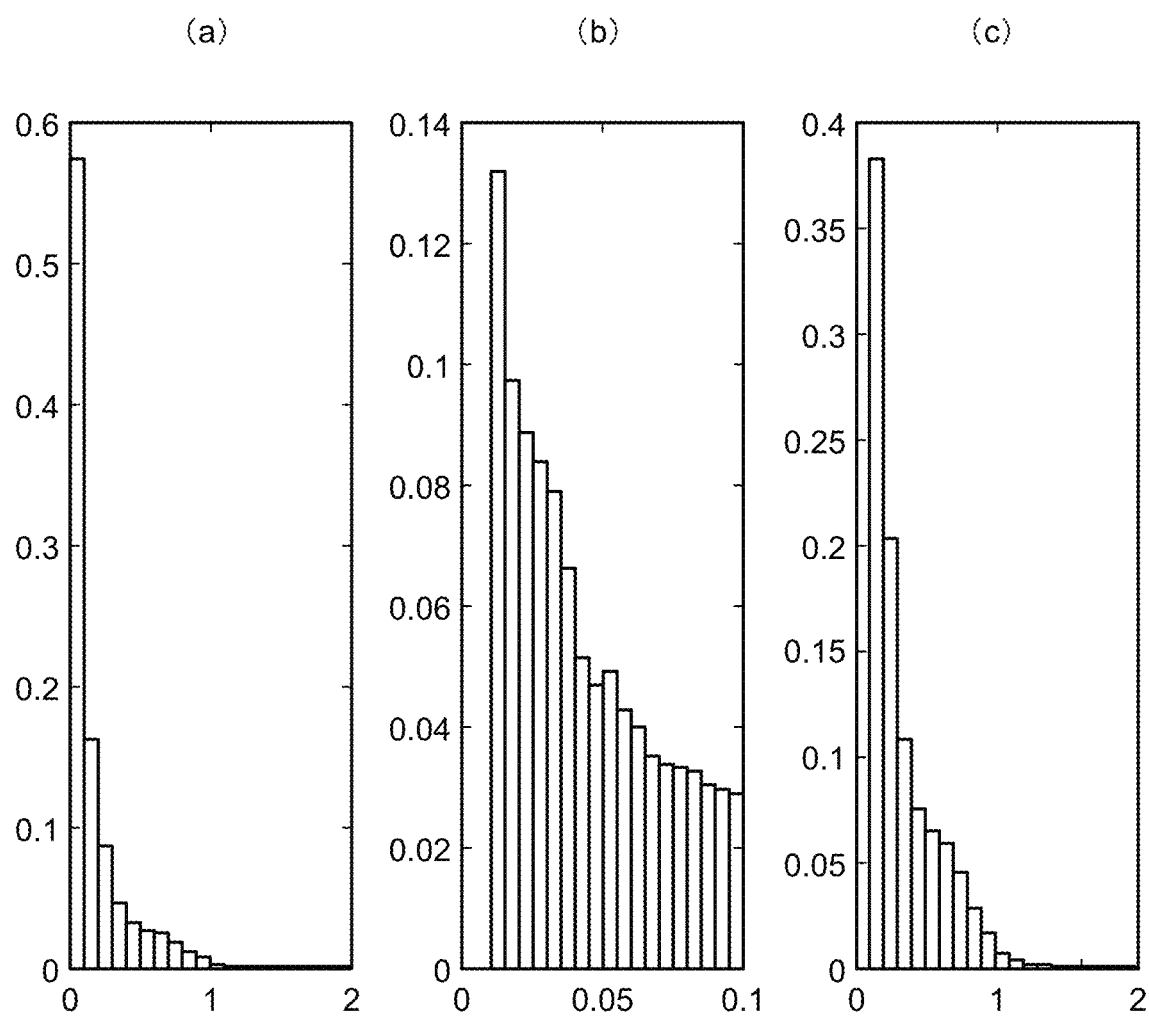
FIG. 21 is a diagram that illustrates a conventional problem.

That is, with the image processing device 3, as it is understood from the comparison between the histogram illustrated in FIG. 12 and the histogram illustrated in FIG. 21, it is possible to remove artifacts that are present in the range of a large quantity of dye from the H corrected dye-quantity image 301 used to extract the H stained area ArH. Thus, application of Otsu's method, or the like, to the histogram of pixel values of the H corrected dye-quantity image 301 enables automatic calculation of a threshold in a desirable manner.

Figure 22:
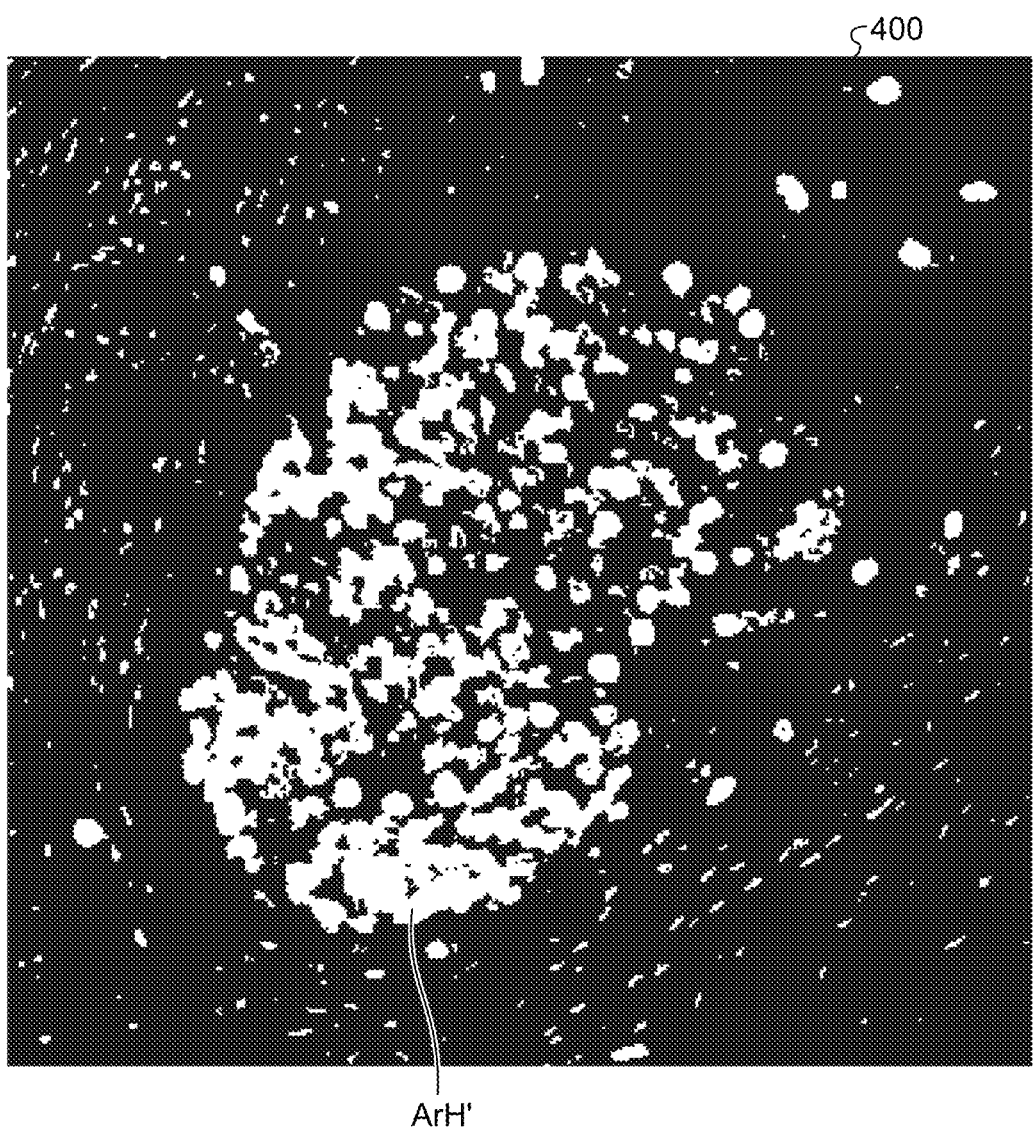
FIG. 22 is a diagram that illustrates a conventional problem.

Therefore, as it is understood from the comparison between the H stained area ArH illustrated in FIG. 13 and the H stained area ArH' illustrated in FIG. 22, the image processing device 3 according to the first embodiment enables extraction of the H stained area ArH in a desirable manner and prevents the positive cell PC from being extracted as the negative cell NC. That is, there is an advantage such that cells are extractable in a desirable manner.

Furthermore, the image processing device 3 according to the first embodiment sets the processing rank of each stain applied to the stained specimen S for an extraction process and a correction process based on specificity information stored in the specificity-information storage unit 333. This allows processing at an appropriate processing rank during an extraction process and a correction process, proper extraction of a stained area, and proper calculation of a corrected dye-quantity image.

Furthermore, to calculate a dye-quantity image, the image processing device 3 according to the first embodiment estimates the spectral transmittance of each pixel from a multiband image by using Wiener estimation, or the like, and estimates the quantity of dye in each pixel with regard to each stain by using the spectral transmittance according to the Lambert-Beer law. This allows high-accuracy estimation of the quantity of dye in each pixel with regard to each stain.

Second Embodiment

Next, a second embodiment is explained.

In the following explanation, the same configuration and step as those in the above-described first embodiment are attached with the same reference numeral, and their detailed explanations are omitted or simplified.

In the above-described first embodiment, an explanation is given of a process of the calculating unit 36 when two types of stains are applied to the stained specimen S.

In the second embodiment, an explanation is given of a process of the calculating unit 36 when three types of stains are applied to the stained specimen S.

Figure 14:
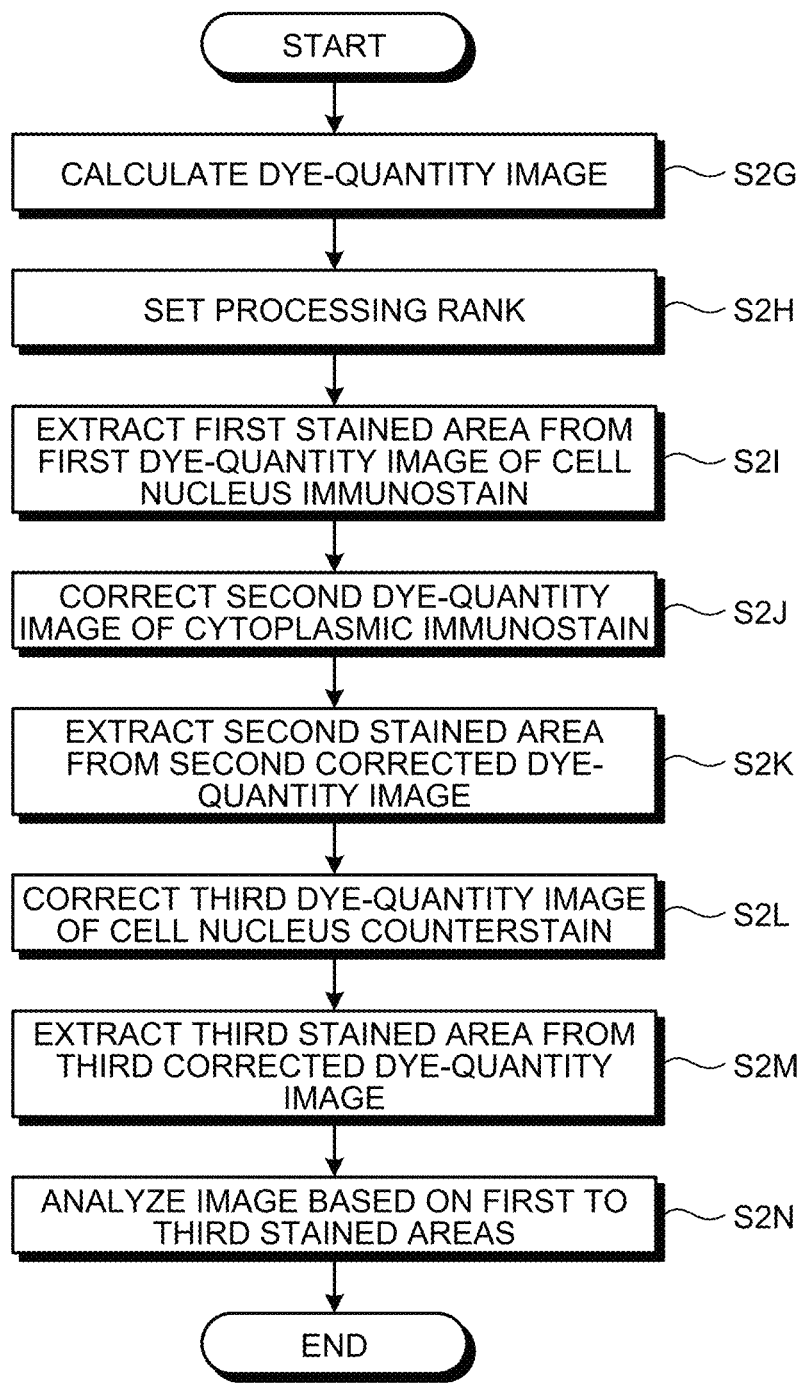
FIG. 14 is a flowchart that illustrates an image processing method according to a second embodiment.
Figure 15:
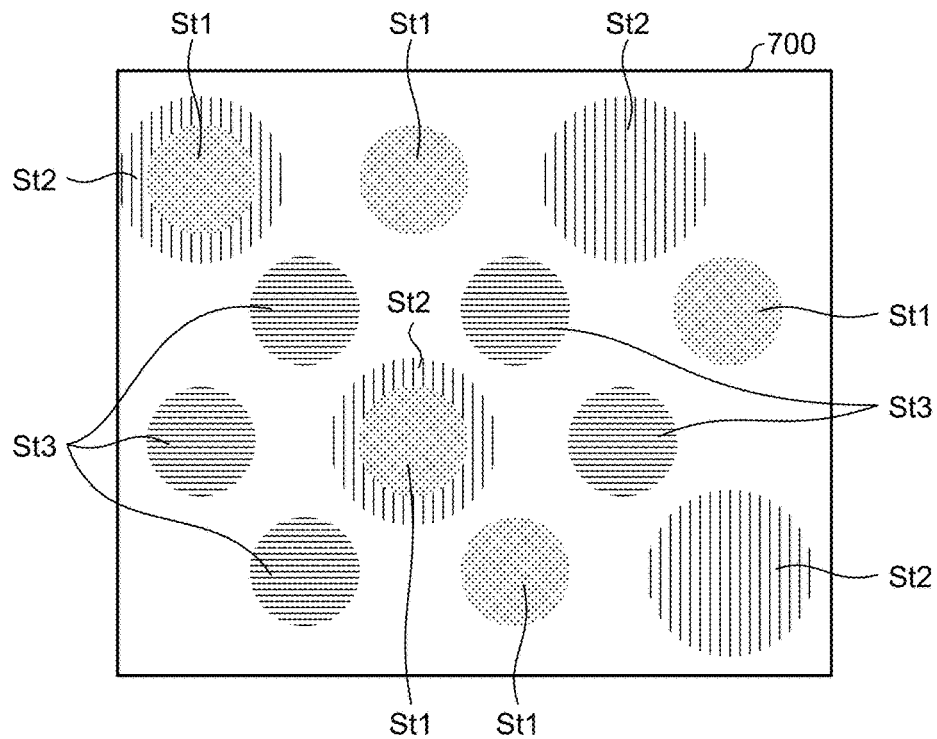
FIG. 15 is a diagram that illustrates an example of a multiband image (stained-specimen image) of the stained specimen to which three types of stains, cell nucleus immunostain, cytoplasmic immunostain, and cell nucleus counterstain, have been applied.

FIG. 14 is a flowchart that illustrates an image processing method according to the second embodiment. Here, FIG. 14 is a flowchart that illustrates the procedure of Step S2, corresponding to FIG. 7. FIG. 15 is a diagram that illustrates an example of a multiband image (stained-specimen image) 700 of the stained specimen S to which three types of stains, cell nucleus immunostain, cytoplasmic immunostain, and cell nucleus counterstain, have been applied.

It is assumed below that three types of stains, cell nucleus immunostain, cytoplasmic immunostain, and cell nucleus counterstain, have been applied to the stained specimen S. Specifically, on the multiband image 700 acquired by the imaging device 2, as illustrated in FIG. 15, for example, there are portions visualized by a cell nucleus immunostain St1, portions visualized by a cytoplasmic immunostain St2, and portions visualized by a cell nucleus counterstain St3.

At Step S2, the single-stain image calculating unit 361 first calculates single stain images each representing the stained state of each of the stains, the cell nucleus immunostain St1, the cytoplasmic immunostain St2, and the cell nucleus counterstain St3, from the multiband image 700 during the same process as that at Step S2A explained in the above-described first embodiment (Step S2G: a single-stain image calculation step). Specifically, at Step S2G, the single-stain image calculating unit 361 calculates a first dye-quantity image (not illustrated) in which each pixel value is the quantity of dye in each pixel with regard to the cell nucleus immunostain St1, a second dye-quantity image (not illustrated) in which each pixel value is the quantity of dye in each pixel with regard to the cytoplasmic immunostain St2, and a third dye-quantity image (not illustrated) in which each pixel value is the quantity of dye in each pixel with regard to the cell nucleus counterstain St3.

After Step S2G, the processing-rank setting unit 365 sets the processing ranks of the cell nucleus immunostain St1, the cytoplasmic immunostain St2, and the cell nucleus counterstain St3 based on specificity information stored in the specificity-information storage unit 333 during the same process as that at Step S2B explained in the above-described first embodiment (Step S2H). Specifically, at Step S2H, the processing-rank setting unit 365 ranks the cell nucleus immunostain (the first stain) St1 as the first processing rank, the cytoplasmic immunostain (the second stain) St2 as the second processing rank, and the cell nucleus counterstain (the second stain) St3 as the third processing rank.

After Step S2H, the stained-area extracting unit 366 performs an extraction process to extract a first stained area Ar1 (see FIG. 16) of the cell nucleus immunostain St1 (the first stain), which is set as the first processing rank by the processing-rank setting unit 365, from the first dye-quantity image of the cell nucleus immunostain St1 during the same process as that at Step S2C explained in the above-described first embodiment (Step S2I: a stained-area extraction step).

Figure 16:
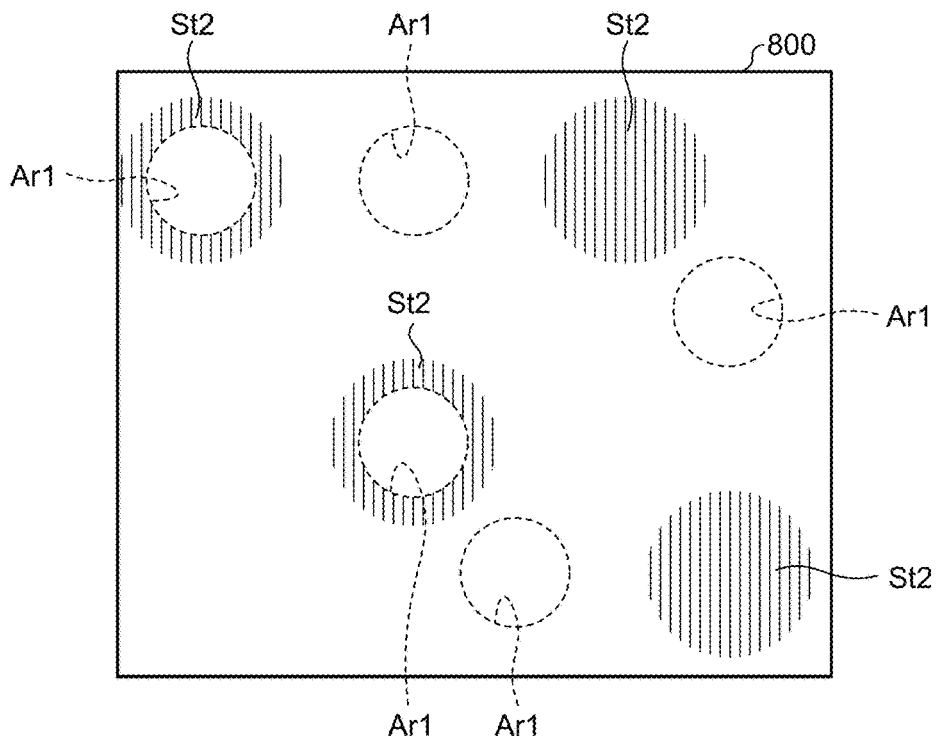
FIG. 16 is a diagram that illustrates an example of a second corrected dye-quantity image that is calculated at a single-stain image correction step S2J illustrated in FIG. 14.

FIG. 16 is a diagram that illustrates an example of a second corrected dye-quantity image 800 that is calculated at a single-stain image correction step S2J.

After Step S2I, the single-stain image correcting unit 367 calculates the second corrected dye-quantity image 800 (FIG. 16) obtained after the second dye-quantity image is corrected by excluding the first stained area Ar1 of the cell nucleus immunostain St1, which is set as the first processing rank by the processing-rank setting unit 365, from the second dye-quantity image of the cytoplasmic immunostain (the second stain) St2, which is set as the second processing rank by the processing-rank setting unit 365, during the same process as that at Step S2D explained in the above-described first embodiment (Step S2J: a single-stain image correction step).

Here, the first stained area Ar1 excluded from the second corrected dye-quantity image 800 is a portion that is not the processing target for the subsequent process (Step S2K).

After Step S2J, the stained-area extracting unit 366 performs an extraction process to extract a second stained area Ar2 (see FIG. 17) of the cytoplasmic immunostain St2 (the second stain), which is set as the second processing rank by the processing-rank setting unit 365, from the second corrected dye-quantity image 800 of the cytoplasmic immunostain St2 during the same process as that at Step S2E explained in the above-described first embodiment (Step S2K: a stained-area extraction step).

Figure 17:
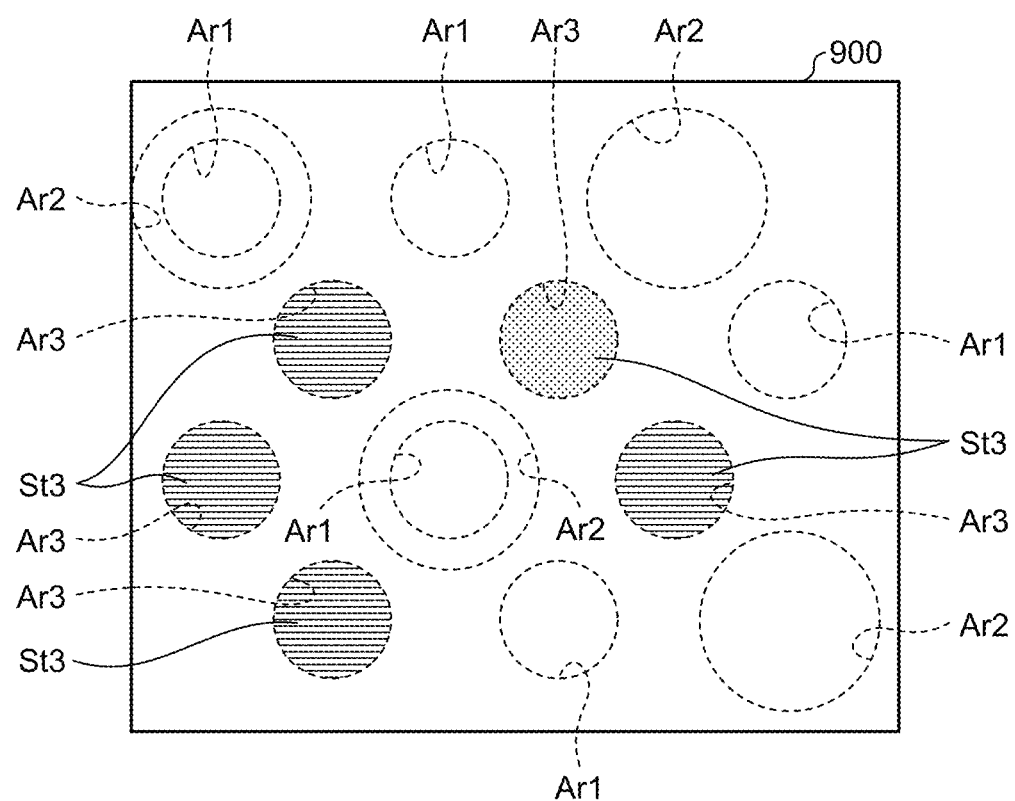
FIG. 17 is a diagram that illustrates an example of a third corrected dye-quantity image that is calculated at a single-stain image correction step S2L illustrated in FIG. 14.

FIG. 17 is a diagram that illustrates an example of a third corrected dye-quantity image 900 that is calculated at a single-stain image correction step S2L.

After Step S2K, the single-stain image correcting unit 367 calculates the third corrected dye-quantity image 900 (see FIG. 17) obtained after the third dye-quantity image of the cell nucleus counterstain (the second stain) St3, set as the third processing rank by the processing-rank setting unit 365, is corrected by excluding the first and the second stained areas Ar1, Ar2 of the cell nucleus immunostain St1 and the cytoplasmic immunostain St2, which are set as the first and the second processing ranks by the processing-rank setting unit 365, respectively, from the third dye-quantity image during the same process as that at the above-described Step S2J (Step S2L: a single-stain image correction step).

Here, the first and the second stained areas Ar1, Ar2 excluded from the third corrected dye-quantity image 900 are portions that are not the processing targets for the subsequent process (Step S2M).

After Step S2L, the stained-area extracting unit 366 performs an extraction process to extract a third stained area Ar3 (FIG. 17) of the cell nucleus counterstain (the second stain) St3, which is set as the third processing rank by the processing-rank setting unit 365, from the third corrected dye-quantity image 900 of the cell nucleus counterstain St3 during the same process as that at Step S2I, S2K (Step S2M: a stained-area extraction step).

After Step S2M, the analyzing unit 368 analyzes the image based on the first to the third stained areas Ar1 to Ar3 in the same manner as Step S2F explained in the above-described first embodiment (Step S2N: an analysis step).

The above-described second embodiment produces the advantage similar to that of the above-described first embodiment even when three types of stains are applied to the stained specimen S.

Other Embodiments

Although the embodiments for implementing the disclosure are explained above, the disclosure does not need to be limited to only the above-described first and second embodiments.

According to the above-described first and second embodiments, dye-quantity images, in which a pixel value is a quantity of dye, is used as a single stain image according to the disclosure; however, this is not a limitation.

For example, at Step S2A3, after the quantity of dye in each pixel is estimated with regard to each stain, a single-stain color reproduction image, in which a pixel value (G*(x)) is an RGB value, is calculated based on the quantity of dye by using the above-described Equations (17) to (26), and the single-stain color reproduction image may be used as a single stain image according to the disclosure. Furthermore, to calculate a single-stain color reproduction image of the target stain, in the above-described Equation (20) and Equation (21), the coefficient $\alpha$ is 1 for the quantity of dye with regard to the target stain, and the coefficient $\alpha$ is 0 for the quantity of dye with regard to other stains.

Furthermore, the average value of bands with regard to the above-described single-stain color reproduction image is calculated, and the obtained gray-scaled image may be used as a single stain image according to the disclosure.

Moreover, a single-stain color reproduction image of each stain, in which a pixel value is an RGB value, is calculated directly based on the pixel value of each pixel of a multiband image by using a look-up table or a transformation matrix, and the single-stain color reproduction image may be used as a single stain image according to the disclosure.

According to the above-described first and second embodiments, at Step S2A3, the spectral transmittance of each pixel is estimated from a multiband image, and the quantity of dye in each pixel is estimated with regard to each stain by using the spectral transmittance; however, this is not a limitation.

For example, the quantity of dye in each pixel may be estimated with regard to each stain directly based on the pixel value of each pixel of a multiband image by using a look-up table or a dye-quantity estimation matrix obtained by regression analysis.

According to the above-described first and second embodiments, the image processing device 3 recognizes the type of stain applied to the stained specimen S based on the metadata attached to a multiband image and, based on specificity information stored in the specificity-information storage unit 333, sets the processing rank of each stain for an extraction process and a correction process; however, this is not a limitation.

For example, the input unit 34 receives input of specificity information as well as the type of stain applied to the stained specimen S in accordance with user's operation. Then, the control unit 32 adds, as metadata, the information indicating the input type of stain and the specificity information to a multiband image stored in the image-data storage unit 332. That is, the processing-rank setting unit 365 sets the processing rank of each stain for an extraction process and a correction process based on the metadata (the information indicating the type of stain and the specificity information). Therefore, with this configuration, the specificity-information storage unit 333 may be omitted.

Furthermore, in accordance with user's operation, the input unit 34 receives input of the processing rank of each stain as well as the type of stain applied to the stained specimen S. Then, the control unit 32 adds, as metadata, the information indicating the input type of stain and the information indicating the processing rank of each stain to a multiband image stored in the image-data storage unit 332. That is, the stained-area extracting unit 366 and the single-stain image correcting unit 367 perform an extraction process and a correction process in accordance with the processing rank described in the metadata. Therefore, with this configuration, the processing-rank setting unit 365 and the specificity-information storage unit 333 may be omitted.

According to the above-described first and second embodiments, the image processing device 3 recognizes the type of stain applied to the stained specimen S based on the metadata attached to a multiband image; however, this is not a limitation.

For example, the type of stain applied to the stained specimen S may be determined based on the color distribution, or the like, of a multiband image.

In the above-described first and second embodiments, the combination of stains applied to the stained specimen S may be not only the combinations described in the first and the second embodiments but also other combinations. Furthermore, there may be four or more types of stains.

According to the above-described first and second embodiments, at Steps S2C, S2E, S2I, S2K, and S2M, Otsu's method, or the like, is applied to the calculated histogram to automatically calculate a threshold; however, this is not a limitation. For example, a fixed percentage, approximately the top 5 to 20%, for the quantity of dye with regard to the whole number of pixels may be used as the threshold.

The image processing device, the image processing method, and the image processing program according to the disclosure produce an advantage in that cells are extractable in a desirable manner.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing device comprising
a processor comprising hardware, wherein the processor is configured to:
calculate each single stain image representing a stained state due to each stain from a stained-specimen image that has captured a specimen to which at least two types of stains are applied;
sequentially perform, on a target stain of all the at least two types of stains, an extraction process to extract a stained area due to the target stain from the single stain image of the target stain, in an order of a stain of the at least two types of stains having high specificity with regard to a target site to a stain of the at least two types of stains having a low specificity with regard to the target site; and
sequentially perform a correction process, on each stain of the at least one type of stain as a second stain except for a first stain, the first stain, having the highest specificity among the at least two types of stains, to correct the single stain image in order of the stain having the highest specificity of the at least two types of stains to the stain having the lowest specificity of the at least two types of stains, wherein
the extraction process comprises extracting the stained area due to each second stain from a corrected single stain image that is obtained after the correction process is performed,
the correction process comprises excluding a predetermined stained area from the single stain image of each second stain,
the predetermined stained area being the stained area that has been extracted by the extraction process before performing the correction process,
the predetermined stained area comprisin, the stained area of the first stain and the stained area of each second stain for which the correction process is performed, and
an image is analyzed with respect to the stained area extracted from the single stain image of the first stain and the stained area extracted from the corrected single stain image of each second stain.

2. The image processing device according to claim 1, wherein the processor is further configured to set, based on specificities of the at least two types of stains, processing ranks of the at least two types of stains for the extraction process and the correction process.

3. The image processing device according to claim 2, further comprising a storage configured to store specificity information indicating the specificities of the at least two types of stains, wherein
the processor is configured to set the processing ranks based on the specificity information.

4. The image processing device according to claim 2, wherein the stained-specimen image has specificity information indicating the specificities of the at least two types of stains attached thereto, and the processor is configured to set the processing ranks based on specificity information.

5. The image processing device according to claim 1, wherein the processor is configured to binarize a histogram of pixel values of the single stain image of the target stain by using a threshold that is any one of a fixed percentage and an automatically calculated value to extract the stained area due to the target stain.

6. The image processing device according to claim 1, wherein, based on the stained area, the processor is configured to count a number of cells stained with the target stain.

7. The image processing device according to claim 6, further comprising a display configured to present at least any one of an image representing the stained area and the number of cells.

8. The image processing device according to claim 1, wherein the processor is further configured to:
estimate a quantity of dye in each pixel with regard to each stain based on the stained- specimen image; and
calculate the single stain image of each stain based on the estimated quantity of dye in each pixel with regard to the stain.

9. The image processing device according to claim 8, wherein the processor is further configured to:
estimate spectral transmittance of each pixel from the stained-specimen image; and
estimate the quantity of dye in each pixel with regard to each stain by using the estimated spectral transmittance.

10. An image processing method comprising:
calculating each single stain image representing a stained state due to each stain from a stained-specimen image that has captured a specimen to which at least two types of stains are applied;
sequentially performing, on a target stain of all the at least two types of stains, an extraction process to extract a stained area due to the target stain from the single stain image of the target stain, in an order of a stain of the at least two types of stains having high specificity with regard to a target site to a stain of the at least two types of stains having a low specificity with regard to the target site; and
sequentially performing a correction process, on each stain of the at least one type of stain as a second stain except for a first stain, the first stain having the highest specificity among the at least two types of stains, to correct the single stain image in order of the stain having the highest specificity of the at least two types of stains to the stain having the lowest specificity of the at least two types of stains, wherein the extraction process comprises extracting the stained area due to each second stain from a corrected single stain image that is obtained after the correction process is performed, the correction process comprises excluding a predetermined stained area from the single stain image of each second stain, the predetermined stained area being the stained area that has been extracted by the extraction process before performing the correction process, the predetermined stained area comprising the stained area of the first stain and the stained area of each second stain for which the correction process is performed, and an image is analyzed with respect to the stained area extracted from the single stain image of the first stain and the stained area extracted from the corrected single stain image of each second stain.

11. A non-transitory computer-readable recording medium recording an image processing program causing an image processing device to implement the image processing method according to claim 10.

12. The image processing device according to claim 1, wherein the first stain is a stain having high binding power with the target site.

13. The image processing device according to claim 1, wherein the firs stain comprises immunostain and the second stain comprises counterstain.

14. The image processing device according to claim 13, wherein the immunostain comprises DAB stain, and the counterstain comprise at least one of ET stain and E stain.

15. The image processing method according to claim 10, wherein the first stain is a stain having high binding power with the target site.

16. The image processing method according to claim 10, wherein the firs stain comprises immunostain and the second stain comprises counterstain.

17. The image processing device according to claim 16, wherein the immunostain comprises DAB stain, and the counterstain comprise at least one of H stain and stain.

18. The non-transitory computer-readable recording medium according to claim 11, wherein the first stain is a stain having high binding power with the target site.

19. The non-transitory computer-readable recording medium according to claim 11, wherein the firs stain comprises immunostain and the second stain comprises counterstain.

20. The non-transitory computer-readable recording medium according to claim 19, wherein the immunostain comprises DAB stain, and the counterstain comprise at least one of H stain and E stain.

* * * * *